US009770205B2

(12) United States Patent
Scheib

(10) Patent No.: US 9,770,205 B2
(45) Date of Patent: *Sep. 26, 2017

(54) METHOD AND SYSTEM FOR MONITORING AND DISPLAYING PHYSIOLOGICAL CONDITIONS

(71) Applicant: Christopher Scheib, Nicholasville, KY (US)

(72) Inventor: Christopher Scheib, Nicholasville, KY (US)

( * ) Notice: Subject to any disclaimer, the term of this patent is extended or adjusted under 35 U.S.C. 154(b) by 277 days.

This patent is subject to a terminal disclaimer.

(21) Appl. No.: 14/513,854

(22) Filed: Oct. 14, 2014

(65) Prior Publication Data
US 2015/0126891 A1 May 7, 2015

Related U.S. Application Data

(63) Continuation-in-part of application No. 12/925,295, filed on Oct. 18, 2010, now abandoned, and a continuation-in-part of application No. 12/925,296, filed on Oct. 18, 2010, now Pat. No. 8,401,631, which is a continuation-in-part of application No. 12/589,047, filed on Oct. 16, 2009, now Pat. No. 8,352,021, which is a continuation-in-part of application No. 12/082,842, filed on Apr. 15, 2008, now Pat. No. 7,720,531.

(60) Provisional application No. 61/889,578, filed on Oct. 11, 2013.

(51) Int. Cl.
A61B 5/048 (2006.01)
A61B 5/0476 (2006.01)
A61B 5/00 (2006.01)
A61B 5/04 (2006.01)
A61B 5/16 (2006.01)

(52) U.S. Cl.
CPC ............ *A61B 5/4821* (2013.01); *A61B 5/048* (2013.01); *A61B 5/04014* (2013.01); *A61B 5/165* (2013.01); *A61B 5/742* (2013.01); *A61B 5/743* (2013.01); *A61B 5/7257* (2013.01)

(58) Field of Classification Search
CPC ... A61B 5/048; A61B 5/4821; A61B 5/04014; A61B 5/165; A61B 5/7257; A61B 5/742; A61B 5/743
USPC ............ 600/300, 544, 545, 26; 340/575–576
See application file for complete search history.

(56) References Cited

U.S. PATENT DOCUMENTS 5,047,930 A * 9/1991 Martens ............... A61B 5/0476
128/920
5,377,100 A * 12/1994 Pope ................... A61B 5/0476
341/20
5,813,993 A * 9/1998 Kaplan ............... A61B 5/0476
600/26

(Continued)

Primary Examiner — Navin Natnithithadha
(74) Attorney, Agent, or Firm — Stockwell + Smedley, PSC

(57) ABSTRACT

Providing an indication of a state of awareness for a patient includes arranging data of an EEG power spectrogram to provide power versus frequency in a log-log arrangement; calculating a first best-fit line for a lower frequency region of the EEG power spectrogram, using a processor; and calculating a second best-fit line for a higher frequency region of the EEG power spectrogram. Also, a display device is used to display a density spectral array of the spectrogram using a display scale that ranges between an upper limit and a lower limit, wherein the lower limit is set based on one of the first best-fit line and the second best-fit line.

18 Claims, 38 Drawing Sheets

(56) References Cited

U.S. PATENT DOCUMENTS

| | | | | |
|---|---|---|---|---|
| 7,720,531 B2* | 5/2010 | Scheib | ............... | A61B 5/048 600/544 |
| 8,352,021 B2* | 1/2013 | Scheib | ............... | A61B 5/048 600/544 |
| 8,401,631 B2* | 3/2013 | Scheib | ............... | A61B 5/048 600/544 |
| 2009/0259136 A1* | 10/2009 | Schieb | ............ | A61B 5/4821 600/544 |
| 2010/0113960 A1* | 5/2010 | Scheib | ............ | A61B 5/4821 600/544 |
| 2011/0118620 A1* | 5/2011 | Scheib | ............... | A61B 5/048 600/544 |
| 2011/0125047 A1* | 5/2011 | Scheib | ............... | A61B 5/048 600/544 |
| 2013/0253362 A1* | 9/2013 | Scheib | ............... | A61B 5/048 600/544 |
| 2013/0317383 A1* | 11/2013 | Scheib | ............... | A61B 5/048 600/544 |
| 2013/0324879 A1* | 12/2013 | Scheib | ............... | A61B 5/048 600/544 |
| 2015/0126890 A1* | 5/2015 | Scheib | ............ | A61B 5/4821 600/544 |

* cited by examiner

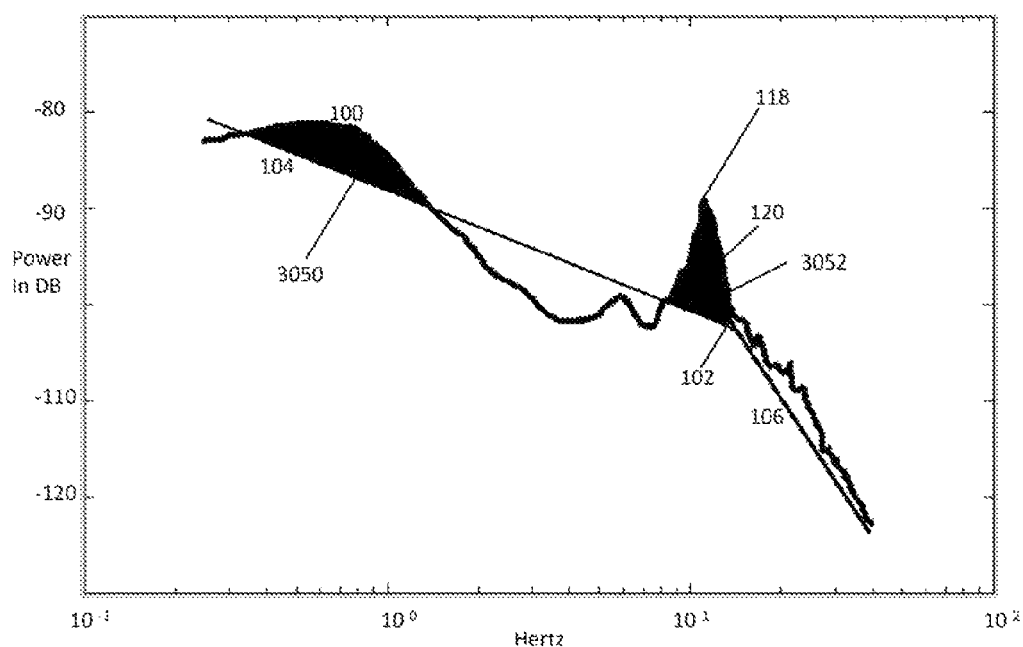

METHOD AND SYSTEM FOR MONITORING AND DISPLAYING PHYSIOLOGICAL CONDITIONS

RELATED APPLICATIONS

The present application is a continuation-in-part of the previously filed U.S. patent application Ser. No. 12/925,295 filed Oct. 18, 2010 and Ser. No. 12/925,296 filed Oct. 18, 2010 (now U.S. Pat. No. 8,401,631), which themselves are continuation-in-part applications of the previously filed U.S. patent application Ser. No. 12/589,047 filed Oct. 16, 2009 (now U.S. Pat. No. 8,352,021) which is a continuation-in-part of the previously filed U.S. patent application Ser. No. 12/082,842 filed Apr. 15, 2008 (now U.S. Pat. No. 7,720,531), the disclosures of which are incorporated herein in their entirety. The present application also claims priority to U.S. Provisional Patent Application Ser. No. 61/889,578, filed Oct. 11, 2013, the disclosure of which is incorporated herein in its entirety.

BACKGROUND

The present invention relates generally to monitoring brain function during different states of consciousness such as general anesthesia, coma or natural sleep and, more particularly, to using electroencephalogram (EEG) data and other physiological data to evaluate brain function.

The definition of the term "anesthesia" is—a lack of awareness—or lack of sensation. For surgical purposes this is generally achieved in two main ways: 1) infiltration of a peripheral or more central nerve bundle with a local anesthesia, which prevents the nerve impulse being processed by the central nervous system and, thus, sensation (of pain or otherwise is not perceived by the individual who remains conscious and aware; and 2) general anesthesia which requires a loss of consciousness in order for the sensation not to be perceived by the individual. To date no systems of monitoring brain function has produced a reference point beyond which one can absolutely state that there exists a complete lack of consciousness at an anesthetic dosage level low enough to be of practical value. Present systems merely produce a measure of probability of loss of consciousness when the anesthetic dosage level is at the low end of the practical range.

The "depth of anesthesia" generally describes the extent to which consciousness is lost following administration of an anesthetic agent. As the magnitude of anesthetization, or depth of anesthesia, increases, an anesthetized patient typically fails to successively respond to spoken commands, loses the eyelid reflex, loses other reflexes, undergoes depression of vital signs, and the like. Once consciousness is lost there is a progression of effects on brain function as higher concentrations or dose of anesthetic agent are administered.

For clinical use, it is desirable to simplify the results of EEG signal analysis of the foregoing, and other types, into a workable parameter that can be used by an anesthesiologist in a clinical setting when attending the patient. Prior techniques have included showing the EEG signal in a relatively unprocessed form or showing a number (or letter) without any other underlying data supporting that number. Neither solution is helpful in a clinical setting; especially, in the case of the "number" indicator, when the number is at best a probability that the patient is not aware or conscious. Ideally, what is desired is a simple indicator that accurately indicates the patient's lack of awareness and how far below the transition to awareness the patient is. The indicator should also account for phenomena that vary by patient such as, for example, the less pronounced a peak of older patients and the possible occurrence of a burst suppression event. Thus, there remains a need for such an indicator that reliably and quickly indicates awareness during general anesthesia and the depth of anesthesia.

SUMMARY

Embodiments of the present invention relate to a method for providing an indication of a state of awareness for a patient includes arranging data of an EEG power spectrogram to provide power versus frequency in a log-log arrangement; calculating a first best-fit line for a lower frequency region of the EEG power spectrogram, using a processor; and calculating a second best-fit line for a higher frequency region of the EEG power spectrogram. Also, a display device is used to display a density spectral array of the spectrogram using a display scale that ranges between an upper limit and a lower limit, wherein the lower limit is set based on one of the first best-fit line and the second best-fit line.

Another aspect relates to providing an indication of a state of awareness for a patient that includes arranging data of an EEG power spectrogram to provide power versus frequency in a log-log arrangement; calculating a first best-fit line for a lower frequency region of the EEG power spectrogram, using a processor; and calculating a second best-fit line for a higher frequency region of the EEG power spectrogram. Providing the indication also includes determining, by the processor, differences between the EEG power spectrogram and the first and second best-fit lines; and displaying, on a display device, the differences between the EEG power spectrogram and the first and second best-fit lines.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Various aspects of a system and method for anesthesia monitoring are illustrated by way of example, and not by way of limitation, in the accompanying drawings, wherein:

FIGS. 30A-30D illustrate DSA display methods in accordance with the principles of the present invention.

DETAILED DESCRIPTION OF THE PREFERRED EMBODIMENTS

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 18:
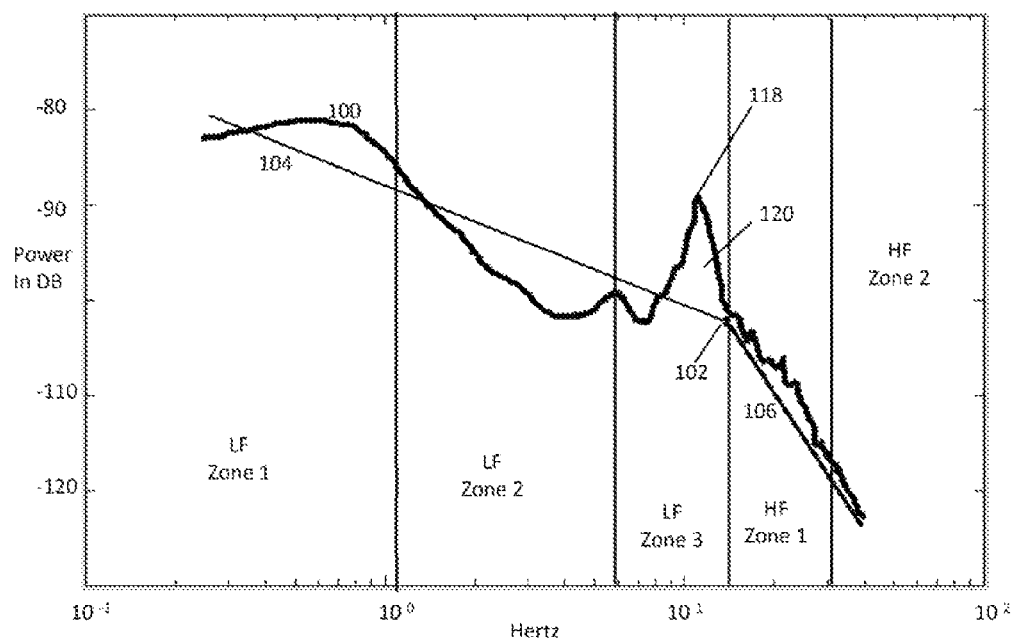
FIG. 18 shows an exemplary log-log EEG power spectrogram in accordance with the principles of the present invention.

In the above-incorporated patent applications the frequency range of contemplated signals extended to about 40 Hz. FIG. 18 shows an exemplary log-log EEG power spectrogram in accordance with the principles of the referenced, incorporated patent application. The spectrogram 100 is that of a patient that is deeply under anesthesia. In other words, the patient has crossed the transition point into a lack of awareness and is relatively far from returning to that transition point. As shown, the power of frequencies above about 12 or 15 Hz significantly drops while the power at the lower frequencies is much higher. In accordance with providing the information in a log-log format, the spectrogram 100 can be transformed into the best-fit lines 104, 106. Regardless of the point of reference from which you measure, the respective slopes of the low frequency line 104 and the high frequency line 106 are vastly different. The intersection point 102 is at about 15 Hz. As noted, this display allows for simple analysis of the anesthetic state, or more generally, the brain function, of a patient.

Additional useful data can be extracted from the graph depicted in FIG. 18. In this graph, an alpha peak 118 is present that would typically be considered an outlier when calculating the best fit line 104. Other peaks may occur in the EEG signal 400 and may be useful as well. One beneficial analysis of such peaks is to use the best fit line 104 as a baseline and subtract it from the signal 100. For the alpha peak 118, for example, the area 120 above the baseline represents information about the alpha peak. For example, its amplitude, its spread, and the center frequency can all be determined by analyzing the area 120.

In practice, the "baseline" (or best fit line or lines) can be subtracted from a log-log spectrum to display peaks that are occurring as described in greater detail below. By doing this at different times, the best-fit spectra method described in the above-identified and incorporated patents and applications can be extended to display what is occurring over time, not simply at a single point in time. Regression analysis of these parameters revealed that there is a correlation between the alpha peak frequency and concentration of the anesthetic agent. Thus, because the alpha peak generally shifts with concentration of anesthesia (decreasing frequency as concentration increases), the changes in the alpha peak can be used as additional information or confirmation when making a determination about the state of awareness of the patient. In some tests, surgical stimulation (e.g., retracting an inflamed nerve root) also resulted in changes of the alpha peak size and location such as reducing the amplitude of the alpha peak and/or shifting it to a higher or lower frequency. These additional factors may be useful when determining the state of awareness of the patient.

However, additional investigation has established that extending the frequency range to about 130 Hz provides beneficial data and analysis as well. Going from 40 Hz to 130 Hz goes beyond what is traditionally thought of as EEG into the EMG range. Similarly, as before, the EEG (and potentially EMG) data is plotted in a log-log representation. This representation and extended frequency range allows more than two best-fit lines to be calculated. For example, the raw data can be modeled by 3, 4 or even more best-fit lines. Once these lines are calculated, analysis of the lines can occur. Within this patent application, the terms EEG and EMG are used for convenience to refer to sensing and collecting physiological responses in the frequency ranges from about 0 Hz to about 130 Hz. Use of these terms is not intended to limit the scope of the present invention to only EEG or EMG machines or techniques but, instead, is intended to encompass sensing of the electrical physiological responses produced by a person within the specified frequency range.

The differences in the heights and slopes of each line, the frequency and amplitude of the intersection points, and the angles formed at the intersections all provide useful data in evaluating brain function.

In addition, the presence and location of various peaks in the log-log data are useful as well. The frequency at which the alpha peak and the delta peak occur, for example, provide useful information for evaluating brain function. When used in conjunction with the best-fit line data, the peak locations provide further certainty that the analysis of brain function is accurate. The area under the peak and a corresponding best-fit line is useful as well. The more the peak spreads or the higher the peak is, generally the more area that will be under the peak which is useful information for evaluating brain function.

In one particular example, there is a correlation between the alpha peak frequency and concentration of the anesthetic agent. Thus, data about the alpha peak (e.g., frequency, height, area, etc.) are indicators of brain function in the presence of an anesthetic agent.

Figure 19:
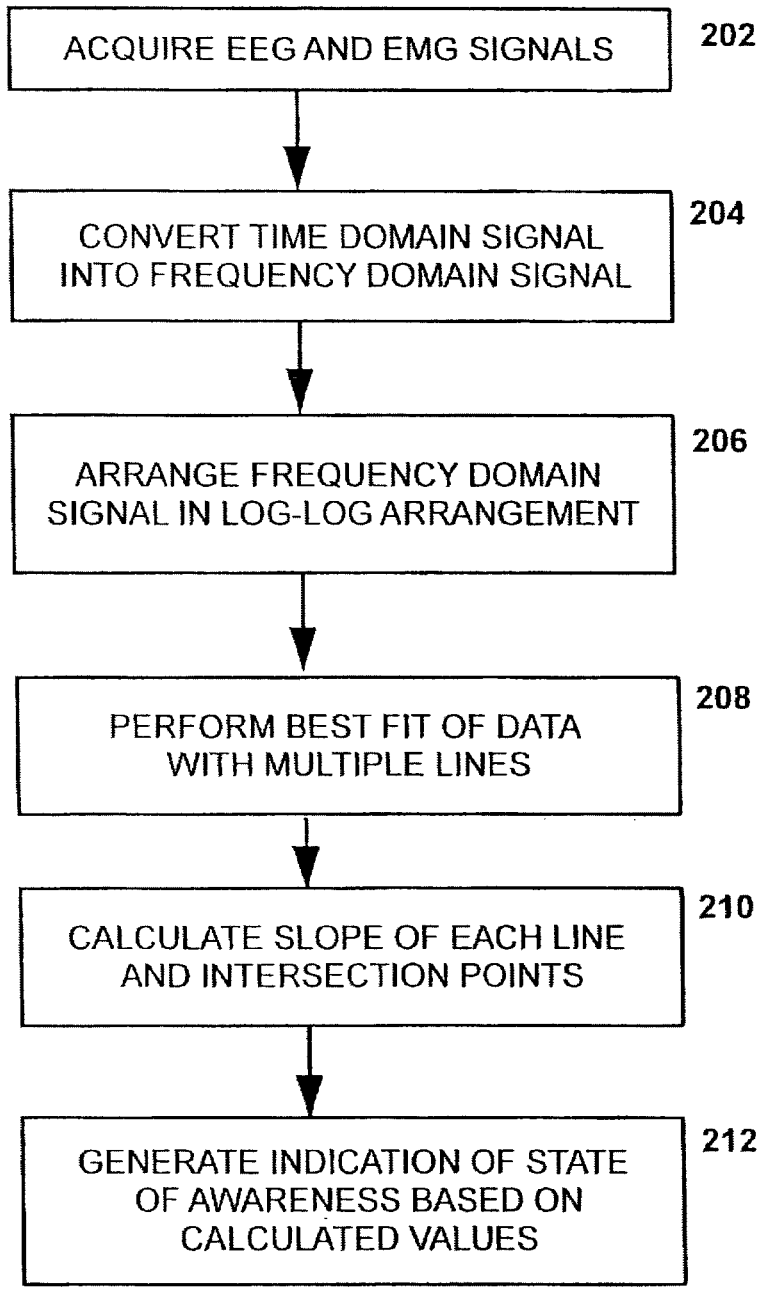
FIG. 19 shows a flowchart of an exemplary algorithm for analyzing EEG spectrograms in accordance with the principles of the present invention.

The flowchart of FIG. 19 depicts an exemplary algorithm for analyzing EEG and EMG spectrograms in accordance with the principles of the present invention. In step 202, the raw EEG signal and EMG signal is captured as is known in the art. For example, signals in the range of approximately 0 to 128 Hz are captured; however, it is contemplated that even higher frequencies may be captured and analyzed as well. Present techniques and devices as well as future-designed EEG and EMG devices may be utilized to acquire the raw signals. Also, as well known in the art, the raw signals may be filtered and processed to reduce noise and to remove artifacts that are known to be introduced into the signals. The raw signal is a time-domain series of samples that are sampled or converted to digital signals which can be then processed by computer platforms or specialized digital signal processors.

Once the digital signals are generated, the time-domain signal can be transformed into a frequency-domain signal in step 204. While there are a number of techniques for converting between the time domain and the frequency domain, a common technique involves the fast Fourier transform method. A number of computationally efficient algorithms for performing fast Fourier transforms beneficially result in a technique that can occur in almost real time with even limited computational power. As one of ordinary skill will recognize, there are a number of parameters that can be selected to control how the transform operates and performs. As an example, in one embodiment of the present invention, a two-second window averaged for periods of about one minute, or even longer, is used to convert the time-domain signal.

One novel realization reached by the present inventor is that the frequency domain signals are visually informative when arranged in a log-log format, in step 206. In particular, the y-axis represents the power, or power spectral density (PSD), of a frequency in the signal and the x-axis represent the frequency. Both axes, though, are scaled logarithmically. What results is a visual display that reveals that the resulting frequency-domain data can generally be split into multiple regions—a first region from about 0 to about 10 or 20 Hz, a second region representing the frequencies above the first (to about 40 Hz); and a third region typically associated with EMG signals between about 40 Hz and 130 Hz. The first range can extend further as well, especially when the patient is in a state of awareness. These regions will be conveniently referred to a low frequency segment, a high frequency segment, and an EMG segment. Those labels are used as a way of convenience and of comparison to each other and are not intended to limit the segments in any way to a particular range of frequencies.

Once the frequency-domain data points are arranged in this log-log format, a best-fit line is calculated in steps 208. In particular, one or more best fit lines are calculated for each segment. One of the easiest best-fit approaches is to use a least-squares approach but one of ordinary skill will recognize that there are numerous other data regression schemes that may be used to approximate a line while minimizing error. In one example, the best fit lines were accomplished using an iterative least-squares approach where the slope and y-intercept of a line providing the minimum mean square between the log of the spectral magnitude and that line were obtained. Also, one of ordinary skill will recognize that optional methods of fitting the data may be accomplished during the least-squares fit as well. For example, points that are statistical outliers can be discarded if their error size suggests that they should not be used when fitting the data to the best-fit line. The best-fit line can then be recalculated with the outliers ignored As mentioned, different regression methods other the least-squares may be used to calculate the best fit lines and furthermore, one regression method may be used for the high frequency line and a different regression method used for the low frequency line and yet a third regression method may be used for the best fit line of the EMG segment.

The determination of when the best fit lines are complete can be accomplished in a number of different ways. The determination can be based on an event in the EEG or EMG signal itself. For example, the EEG signal may exhibit an alpha-peak at a certain frequency and that value is used for the endpoints of the two best-fit lines of the high and low frequency segments. For example, the first best-fit line is calculated from the lowest frequency to the alpha-peak frequency and the second best-fit line is calculated from the alpha-peak frequency to the highest frequency. The alpha-peak frequency, itself, can be selected in different ways such as at the beginning of the peak, a center frequency, or at the end of the peak. Alternatively, the decision to stop the least-squares fitting can be determined on the fly as the best-fit lines are being calculated. For example, an analysis can be made to determine when a similar frequency is reached from both directions at which both the first best-fit line and the second best-fit line start deviating significantly (e.g., some percentage, such as, for example 3% to 8%) from the previously calculated best-fit line. This frequency, then, is the dividing point between the two best-fit line segments.

Once the best-fit lines are determined, then the slope of each line can be calculated and the intersection point as well with the neighbor segment (see step 210). Of particular interest is the frequency at the intersection point. Based on the relative slopes of the best-fit lines and the frequency of the intersection points, an indication is generated, in step 212, that relates to the state of anesthesia, or the state of awareness, of the patient.

Figure 20:
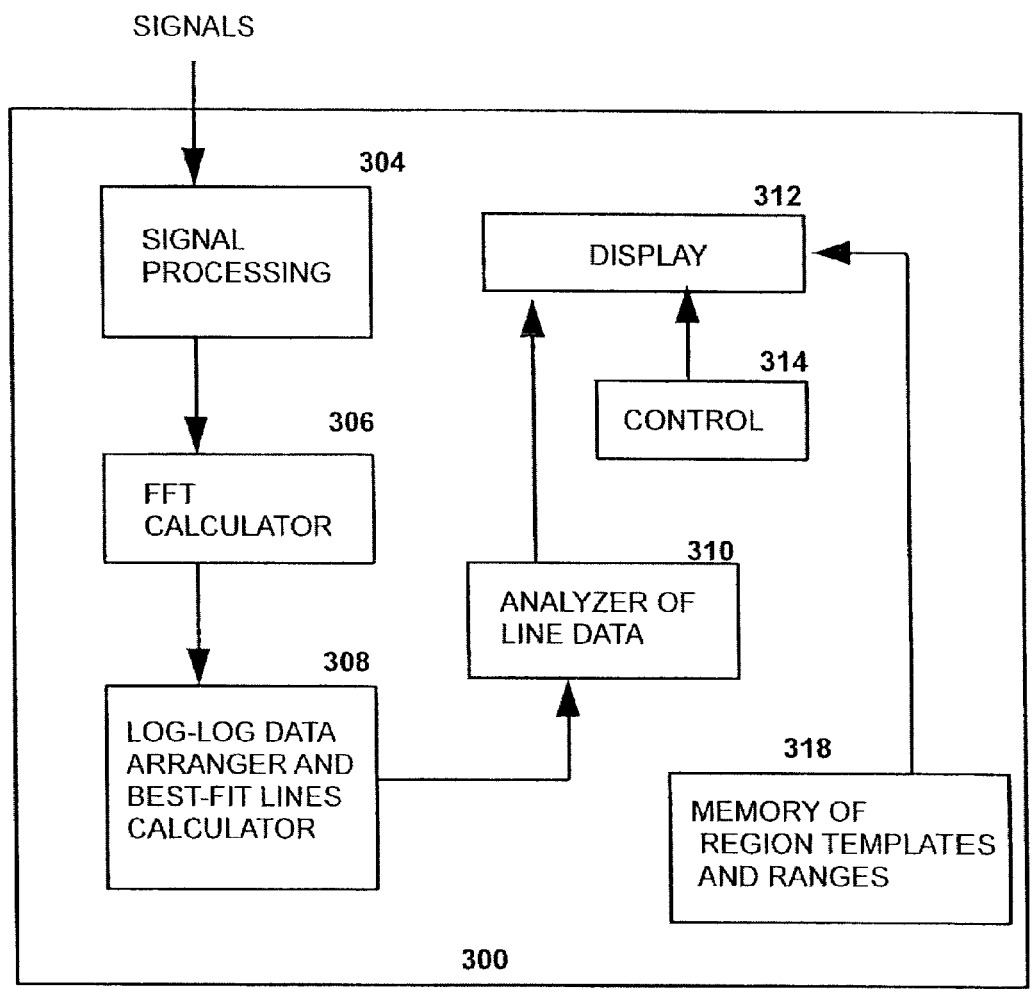
FIG. 20 shows an apparatus on which the flowchart of FIG. 19 may be performed in accordance with the principles of the present invention.

FIG. 20 illustrates an automated platform on which the algorithm described above may be implemented. In practice, the device 300 would be used during surgery to monitor the anesthesia state of the patient to allow an anesthesiologist to modify the delivery of an anesthetic agent as appropriate. The device 300 is shown in functional block form in FIG. 20 because the different functional blocks may be implemented in a variety of ways without departing from the scope of the present invention. For example, a programmable computer with a typical microprocessor may implement a variety of the functions in software programs that are stored on an accessible media and executed during operation. Alternatively, some of the functions may be implemented using specialized hardware including DSP chips and microcontrollers. One of ordinary skill will recognize that various combinations of hardware and software may be utilized to accomplish the functions of the blocks shown in FIG. 20.

The EEG and EMG signals 302 are received and then filtered and converted by a signal processor 304. That signal can then be transformed into the frequency domain by a fast Fourier transformer 306. The power spectrum of the frequency domain signal can then be calculated in a log-log arrangement so that an interpolator 308 can calculate multiple best-fit lines for the spectrum. An analyzer 310 analyzes the best fit lines to determine their respective slopes and the frequency at which they intersect.

Based on the calculations of the analyzer 310 a display 312 provides an indication of the anesthesia state of the patient. The display 312 may be multifaceted to provide the viewer of the display with different information. Two particularly relevant pieces of data are a) the difference between the slopes of the best-fit lines and b) the frequency at which the lines intersect. Thus, these values may be displayed as raw numeric information. A graphical display may be included which graphs these values in a historical fashion so that the viewer of the display can see how the values have been changing in some preset time period. For example, the display could show the values over a window depicting the last 5 minutes. A control 314 for the display 312 can be used to allow the viewer to change between different formats of output as desired. The display 312 can also be configured to display the best-fit lines in near real-time with (or without) the additional values discussed above.

There is a memory 318 that stores the values for different region templates based on patient parameters (e.g., sex, age, drug use, head injury history, etc.). Using these patient factors, an appropriate template is also displayed along with the best fit lines and/or the raw EEG signal in order to give the clinician additional confirmation of suspected spindle activity. The display of the template having these three (or more) angular sections can be accomplished in a variety of ways. For example, the colors of the regions (e.g., red, yellow, green) can be used to provide additional visual clues regarding the patient's condition. For example, if the best-fit line is in the lower region, then the background of that section of the display can be green. If the best-fit line is in other angular sections of the template, then the background of those sections can be red or yellow. In this way, the clinician can be alerted by simply seeing which color is being displayed in the higher frequency region of the display.

Also, (not shown) the device 300 may included a storage function that records various signals and calculations during the duration of the surgery.

Other aspects of the present invention include filtered time domain EEG. (display and use for analysis). "Raw EEG" displays are filtered but over a broad range such as >1 Hz and <100 Hz and a 60 Hz notch filter. However, a more narrow filtered time domain allows the clinician to see the oscillation that creates the alpha peak without the interference of either low frequency baseline changes or high frequency EMG noise. It also enables the clinician to verify the interpretation of the spectrogram.

For example, one filtered signal could include a display in the operating room of narrow range filtered time domain signal such as 7-14 Hz to show the spindle oscillation. A declining amplitude of this oscillation indicates either light or deep anesthesia.

Other examples include multiple filtered ranges to show changes in other oscillations. This can help with interpreting changes in the spindle oscillation.

Additionally, the filter widths can be adjusted to capture the activity of a changing peak width and center frequency (and the changing values over time of the width height and center frequency of the peak controlling the filter.)

Essentially, the filtering of the signals can accomplish filtering out of the EMG noise. The spectral data itself of the signal can be used to determine what type of filtering will occur. In particular, the location and amplitude of one or more of the peaks (and their shape) can be used to determine how filtering takes place.

Figure 21:
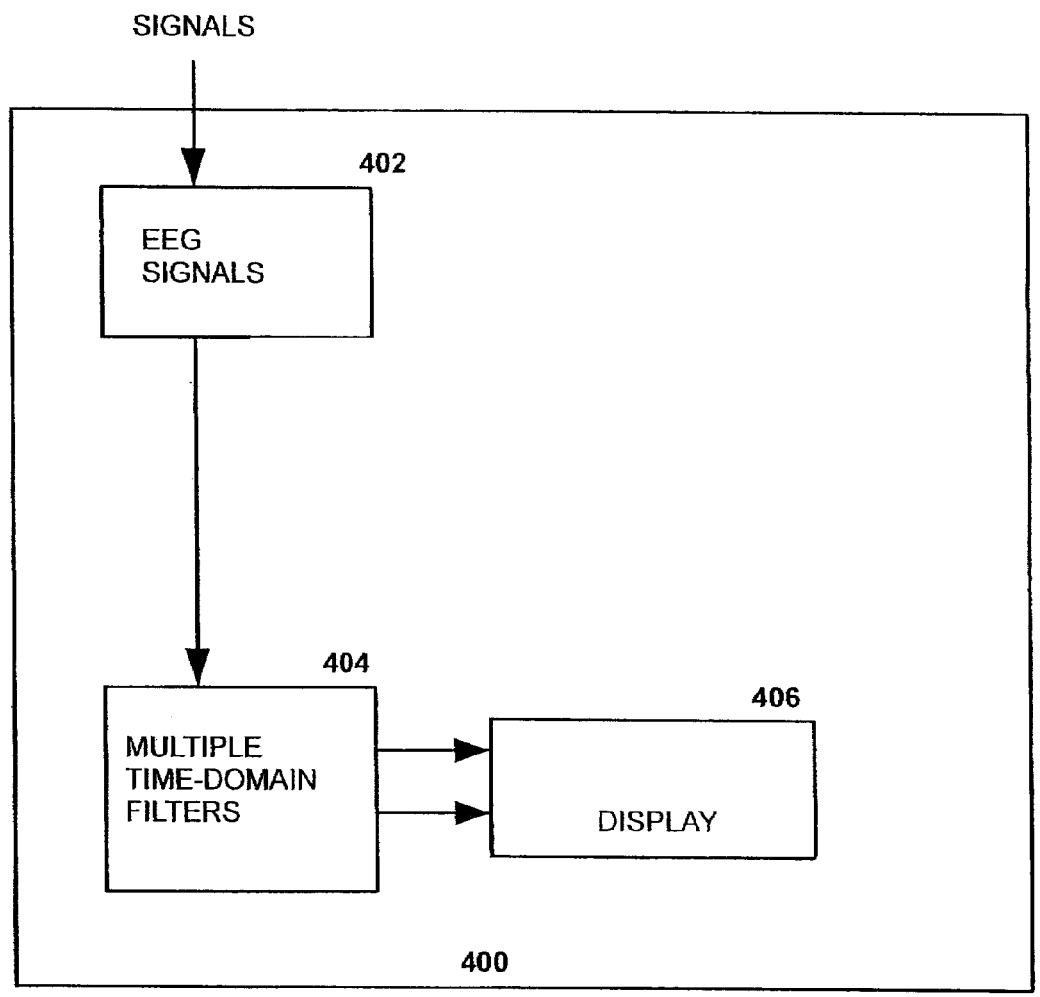
FIG. 21 shows an apparatus which may operate in accordance with the principles of the present invention.

FIG. 21 illustrates an automated platform on which the filtering functions described above may be implemented. In practice, the device 400 would be used during surgery to monitor the anesthesia state of the patient to allow an anesthesiologist to modify the delivery of an anesthetic agent as appropriate. The device 400 is shown in functional block form in FIG. 21 because the different functional blocks may be implemented in a variety of ways without departing from the scope of the present invention. For example, a programmable computer with a typical microprocessor may implement a variety of the functions in software programs that are stored on an accessible media and executed during operation. Alternatively, some of the functions may be implemented using specialized hardware including DSP chips and microcontrollers. One of ordinary skill will recognize that various combinations of hardware and software may be utilized to accomplish the functions of the blocks shown in FIG. 21.

The EEG signals (analog) are received and initially filtered in a receiver 402. For example, the raw signals can initially be filtered such that signals from about 1 Hz to about 100 Hz are analyzed. Other ranges of frequency filtering can be used as well without departing from the scope of the present invention. Next, this signal can be fed to multiple time-domain filters 404. For example, there can be a filter that passes only the alpha waves, another filter that passes only the beta waves, another filter that passes on the gamma waves, and another filter that passes only the delta waves. The different filtered waveforms can then be displayed visually on a display 406.

Frequency domain methods require 30 to 60 seconds to assess the EEG spectrum. The time domain can give instant information that the situation has changed. Currently utilized time domain methodology is a single unfiltered "raw" EEG signal. Multiple neurophysiologic processes can occur simultaneously making the "raw" signal difficult to interpret. Multiple filtered displays can help to identify the different processes and create an indication of the neurophysiologic state.

One such process is the spindle oscillation. Verification that this process is occurring can indicate that the patient is in an unconscious state. To verify the spindle it is useful to have displays that are filtered to exclude activity outside of the spindle range which is 7-14 Hz. One display is at a sufficient speed to identify oscillations that have a wavelength of about 100 msec. One inch per second is a good example. Since the spindle oscillations occur in packets with gaps in between packets (not a continuous oscillation) it is useful to have a second window at a speed that is about one inch per ten seconds. A third display that shows the trend for long periods of time is also useful.

Another process worth monitoring with a filtered time domain display is the gamma band which is above 25 Hz and extending to 40 or 50 Hz. Increased activity in this frequency range could indicate that the patient is becoming aware. (Gamma could also be EMG.) Arranging gamma band windows at the same speed as the alpha band displays is useful to create an indication of the neurophysiologic state. Having the different frequency bands arranged one frequency directly above the other helps to make the assessment. Packets of spindles do not begin and end at the same time as packets of gamma band activity. Burst suppression is a neurophysiologic state where packets of oscillations begin at the same moment at multiple frequency bands. Burst suppression is usually identified by the periods of electrical silence (suppression). However, there can be continuous bursting with few or no periods of electrical silence. When that occurs the multiple filtered band displays are useful to identify bursting from spindling.

The filtering and display of the different time domain bands utilize different display window sizes (in the time dimension) and different frequency bands. For example, the display of the alpha wave signals in one window may show a 2 to 4 second snapshot of the wave while another display shows about a 30 second snapshot of the same wave. In this way, the clinician can see the current activity of a particular frequency band as well as the recent trend of that frequency band. A third window can be used to display the historical trend of a particular frequency band since a procedure was started.

In at least one embodiment, the different frequency bands are shown in separate windows while in other embodiments, the signals of the different frequency bands can be superimposed within the same window.

Figure 22:
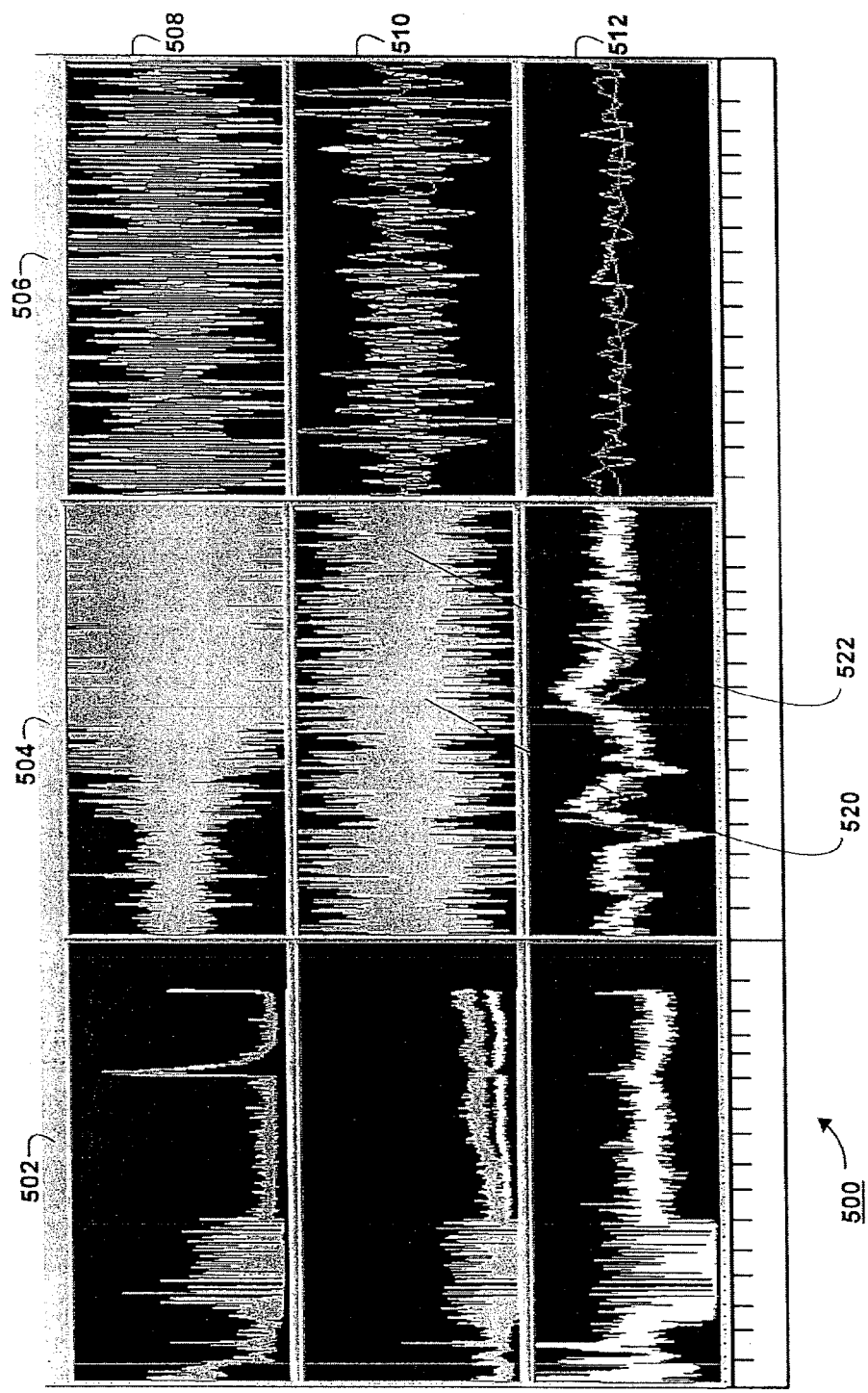
FIG. 22 illustrates an exemplary display in accordance with the principles of the present invention.

FIG. 22 illustrates an exemplary display in accordance with the principles of the present invention. The display 500 is an example only and is not intended to limit the present invention to a 3×3 grid of windows. In general, the display 500 shows that multiple frequency bands of EEG time domain signals are displayed in windows having different time scales. In addition, the different waveforms can be shown in different colors so as to visually distinguish each signal from another.

In FIG. 22, there are three different time scale windows represented by the columns 502, 504 and 506. The physical size of the apparatus which presents the display 500 plays a factor but typically the time scales for the different windows are chosen to provide useful, visual information to a clinician. For example, alpha waves range from about 7 Hz to about 14 Hz, so a two second window (column 506) displays the individual cycles of the alpha waves. However, a 30 second window of about the same size (as depicted in column 504) will show packets of alpha wave peaks rather than the individual cycles themselves. A third time value window 502 can show a long period of time so that the trend or RMS power, or peak-to-peak values, of a signal can be evaluated. More than one frequency band can be trended in the third column. If the alpha band has more amplitude than the theta band, then it indicates that there is a peak in the alpha range. This can be used to help locate the point where the spindle peak is at the maximum. For this purpose, tracking the highest point in the alpha range and the lowest point in the theta range provide the most benefit. Similarly, the beta range can also be tracked to detect a beta peak.

The rows 508, 510, 512 of the display 500 represent different frequency bands. For example, the top row 508 can show delta or theta waves or might even show the raw EEG signal. The second row 510 can show the alpha wave band and the bottom row 512 can show another frequency band such as the gamma waves. Thus, each row can represent a different frequency band of the EEG signal. Of course one of ordinary skill will appreciate that the positions of the different bands can vary; for example, the bottom row 512 can be used to display the raw EEG signal and the top row 508 could be used to display the gamma band or some other frequency band. In addition, it is beneficial to superimpose different frequency bands over one another as well. For example, the middle window shows two signals 520, 522 having different colors. If for example, the white signal 522 is the beta wave band and the gray signal 520 is the alpha wave band, then the amount of the different colors that are visible will visually alert a clinician when the beta activity is increasing and the alpha activity is decreasing. Thus, there is an indication to the clinician that the patient may be awakening or that the there is little fear of the patient awakening. Alternatively, the two bands could be the alpha band and the theta band and the visual information provided by the two colors could reveal spindle activity.

There are at least two concepts for utilizing the electroencephalogram (EEG) for monitoring and understanding the mechanism of anesthesia. One concept is to use mathematical processes to extract a parameter which is presumed to correlate with the amount of anesthetic effect. This is the quantitative EEG or "qEEG" approach. The mechanism of anesthesia which this parameter is presumed to correlate with is a progressive dysfunction of the brain. The original brain dysfunction or depression theory was Meyer-Overton which proposed disruption when ether dissolved in the lipids of neuron membranes. Today the depression theory is that anesthetic agents affect ion channels enhancing inhibitory and reducing excitatory synaptic processes.

An alternative view is that the EEG contains signals created by oscillatory processes in the thalamus and cortex. These thalamocortical oscillations, in particular spindle oscillations, occur during natural slow wave sleep. There is evidence that anesthetic agents affect ion channels that control these natural thalamocortical oscillations in ways that prevent the natural wake-up processes from terminating the oscillations. Spindle oscillations are not compatible with consciousness but are not brain dysfunction or brain depression. They imply a functional state that is different from the functional state of the brain which creates consciousness. Spindle oscillations are not a total mechanism of anesthesia. They may occur after loss of consciousness and be terminated before return of consciousness. Thalamocortical oscillations are not a mechanism of surgical immobility. However, detecting spindle oscillations during anesthesia may be a reliable way to insure a lack of awareness for individual surgical patients.

The proposed method for detecting spindle oscillations in the EEG during anesthesia is to evaluate the shape of the EEG spectrum on a log-log graph. In this presentation the EEG spectrum can be approximated by two straight lines. The low frequency approximation line has a shallow slope and a peak in the 7-14 Hertz range rises above it that results from spindle oscillations. The high frequency approximation line has a steep slope. This is the shape that occurs in the anesthetic range with maximum spindle activity. If the anesthetic agent concentration is increased or decreased, the shape of the spectrum will change in predictable ways. The limited number of, and the consistent progression of log-log EEG spectral shapes enables an alternative to the parameter approach. This alternative is an EEG spectral feature analysis method which could be called "visual qEEG". The patient's log-log EEG spectrum would be compared to a library of spectra from other patients to determine the anesthetic state. Also, the patient's EEG spectra can be recorded during the procedure and used for comparison to track changes in the anesthetic state.

Applicants recognize that there is a conventional EEG "CSA" (compressed spectral array) display. At regular time intervals a new spectrum (log-linear) is produce at a set distance below the previous one. The process is repeated until the top spectrum scrolls off the display. What happens is a new spectrum is produced at the same spot and the previous spectra scroll up. However, such a display is different than the presently contemplated invention in that the conventional display does not permit useful comparisons between different spectra and, in particular, does not permit comparison of the amplitudes of different spectra.

Thus, according to certain embodiments of the present invention, the EEG spectrum on a log-log graph can be used (with or without approximation lines or drawing lines on the background) with another spectrum for comparison. The other spectrum can be from the same patient recorded earlier in the procedure. The other spectrum can be from another patient. A spectrum from another patient can be adjusted to compensate for differences in amplitude. The approximation lines can be used to compensate for differences in amplitude. Also, the other spectrum can be an average spectrum of a number of other patients and, in particular, the other patients can be selected so as to have similar age, gender, demographic, or medical profiles that are similar to the patient. Thus, the reference spectrum may be an actual spectrum observed for that patient, or another patient. The reference spectrum can also be an artificial construct that statistically combines different spectra that are relevant. Additionally, the reference spectrum can be a scaled version of another spectrum to account for amplitude differences or other variations. These reference spectra can be stored in computer-accessible memory and local processing can retrieve them as is for display or can combine them to form a reference spectrum. For example, parameters about the current patient such as age, sex, drug use, lifestyle habits, health history, etc. can be input so that a reference spectrum can be customized from a library of reference spectra depending on each particular patient.

A major goal of a quantitative EEG (qEEG) method is to indicate the level of anesthesia. Current qEEG methods have been demonstrated to fail at this fundamental requirement. Our research has found a simple reason for this failure and explains what must be done to succeed.

Current qEEG methods rely on a single spectra or time period from the subject. Since the amplitude of the EEG signal at equivalent levels of anesthesia varies between subjects due to difference between subjects in the strength of the signal at its source and resistance between the source and the electrodes which detect it, they rely on a ratio of amplitude or power between two or more frequency bands to indicate the level of anesthesia. Our research demonstrates that there is a significant range of level of anesthesia where the pattern of the EEG spectra does not change and, therefore, that amplitude ratio between two or more frequency bands does not change. This results in those current qEEG methods inaccurately indicating the level of anesthesia. Our research reveals that even though the amplitude ratio may not be significantly changing, the overall amplitude or power goes up or down with the agent concentration.

In order to accurately indicate the level of anesthesia for an individual patient with a qEEG method one can obtain a series of EEG spectra at different known or calculated levels from that patient and compare them with each other for amplitude and compare them with each other and with EEG spectra from other patients for the shape of the spectra. One can then identify an EEG spectrum in the set of spectra obtained from the patient that can be used as a reference point and the pattern of change over a moderate range of level of anesthesia. We can extrapolate beyond the boundaries of the levels that we measured in our patient with the data from the set of similar EEG spectral patterns. For example, 2, 3, or 4 spectra from our patient can be matched with rising or falling anesthesia agent concentration to a similar number of spectra from a series of rising or falling agent concentration in one set of spectra a (individual, group, or average of several individuals) out of many sets in the library. In the area where the overall amplitude changes without a change in shape of the spectra, those spectra are not the best candidates for selection as a reference. However, when the shape begins to change with changing level of anesthesia agent then we can select that spectrum as a reference point spectra. The extrapolation occurs in that if our patient behaves like the group over the agent level range where we measured, then he will likely behave the same as we extend out of the range.

Once that reference EEG spectrum and pattern of change are found, subsequent changes in the EEG spectra of that patient can be used to indicate the current level of anesthesia.

Another problem with current qEEG methods is that they rely on specific frequency ranges. Our research has determined that the EEG spectral pattern changes that occur as the level of anesthesia changes do not "pivot" at the exact same frequency ranges for all patients. The EEG spectral patterns do change in ways that are similar for almost all patients but the exact boundaries of the defining frequency ranges vary between patients and shift with the level of anesthesia. These variations should be accounted for in order to be able to use the EEG spectra as an indication of the level of anesthesia for an individual.

The series of EEG spectral patterns that occur for any given patient over the range of levels of anesthesia will usually be very similar (e.g., best-fit approximated lines in different frequency bands) to the series that occurred for a group of similar patients receiving the same anesthetic agents. The number of EEG spectral pattern series that occur is small enough to be used by the method briefly described above but large enough to create inaccuracy in currently used qEEG methods.

An apparatus obtains a series of EEG spectra from a patient at different levels of anesthesia and compares them to each other and a library of sets of EEG spectra. The level of anesthesia could be entered manually or automatically from the patient monitoring system and could involve calculations to determine the level. As mentioned above, for example, 2, 3 or 4 "reference" spectra may be beneficial to performing the methods discussed herein; however one of ordinary skill will recognize that fewer or more spectra could be obtained without departing from the scope of the present invention."

Next, a set that best matches is found for the series from this patient. Features of a Log-Log spectrum that can be used to "measure" similarity may for example include a high-frequency line, a low-frequency line, an intersection point between the two, the two peaks in a low-frequency area, and a trough point between the two peaks. As mentioned, these features do not have absolute and unvarying frequency ranges. Their frequency ranges may vary with anesthetic and between patients.

A determination is made, based on changing spectra shape, of a spectrum from our patient that can be used as a reference point for level of anesthesia to correspond to a similar point in the best match set. By finding that reference point spectra and knowing the changes that occurred in the set of similar patterns from other patients we can determine the level of anesthesia in our patient from the EEG spectral shape and amplitude. We can extrapolate beyond the boundaries of the levels that we measured in our patient with the data from the set of similar EEG spectral patterns.

One of ordinary skill will recognize that an end result could involve a display of spectra, a graphic related to the spectra, or a number or some other indication of the level of anesthesia that was mathematically derived with the aid of the EEG spectral comparisons.

There is evidence that there is a relation between an anesthetic agent concentration and the maximum peak in the alpha (7-14 Hz) range. Changing the anesthetic agent concentration from that point changes the spectrum in predictable ways. Increasing produces one sequence of changes and decreasing produces a different sequence. In general, the maximum spindle point can be a reference in the progression of spectral changes with changing agent concentration. Both higher concentrations and lower concentrations will result in a smaller spindle peak. Thus, a patient's maximum spindle point can be used to determine the patient's sensitivity to anesthetic agents.

Also, the use of multiple filtered bands of signals discussed previously can be extended by using a mathematical approach to quantify the number and amplitude of the individual cycles within a spindle and the number of spindles in a unit of time or the time interval between spindles. These values can be used to determine the state of awareness of the individual. For different patients, the number of spindles, their spacing, and their amplitude may vary and thus previous data for that individual, or similar individuals, may be used in conjunction with the raw data to determine the state of awareness of the individual.

In the patents and patent applications identified above as being incorporated by reference, a central theme is that the shape and amplitude of the EEG spectra is a useful indicator of the anesthetic state. It takes 30-60 seconds to create an accurate EEG spectrum. A faster time domain method that can give an indication that the spectrum is stable, changing, or changing in a particular direction is beneficial as well.

Figure 1:
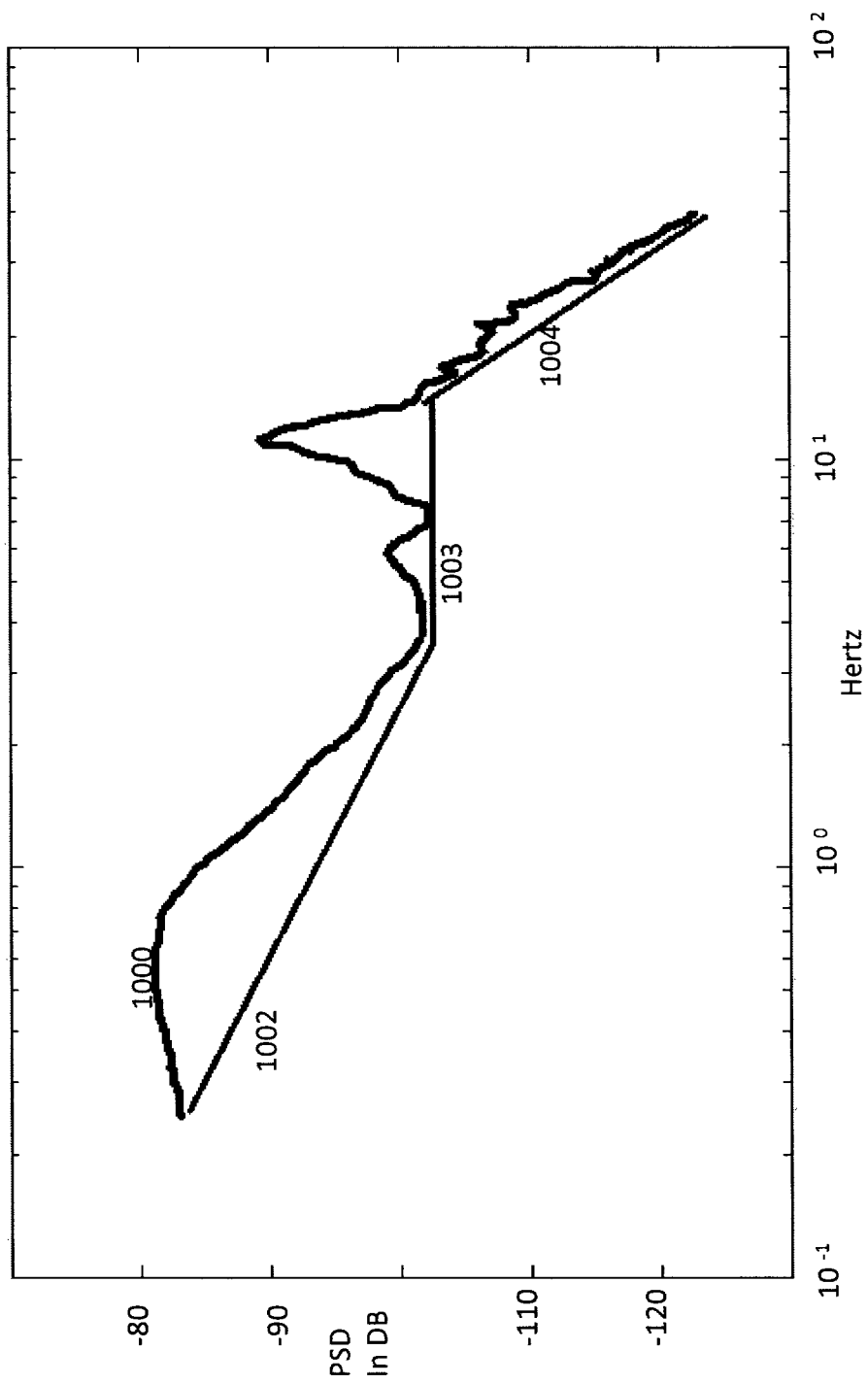
FIG. 1 illustrates a log-log spectrum of the EEG of a patient that is at an adequate level of anesthesia.
Figure 2:
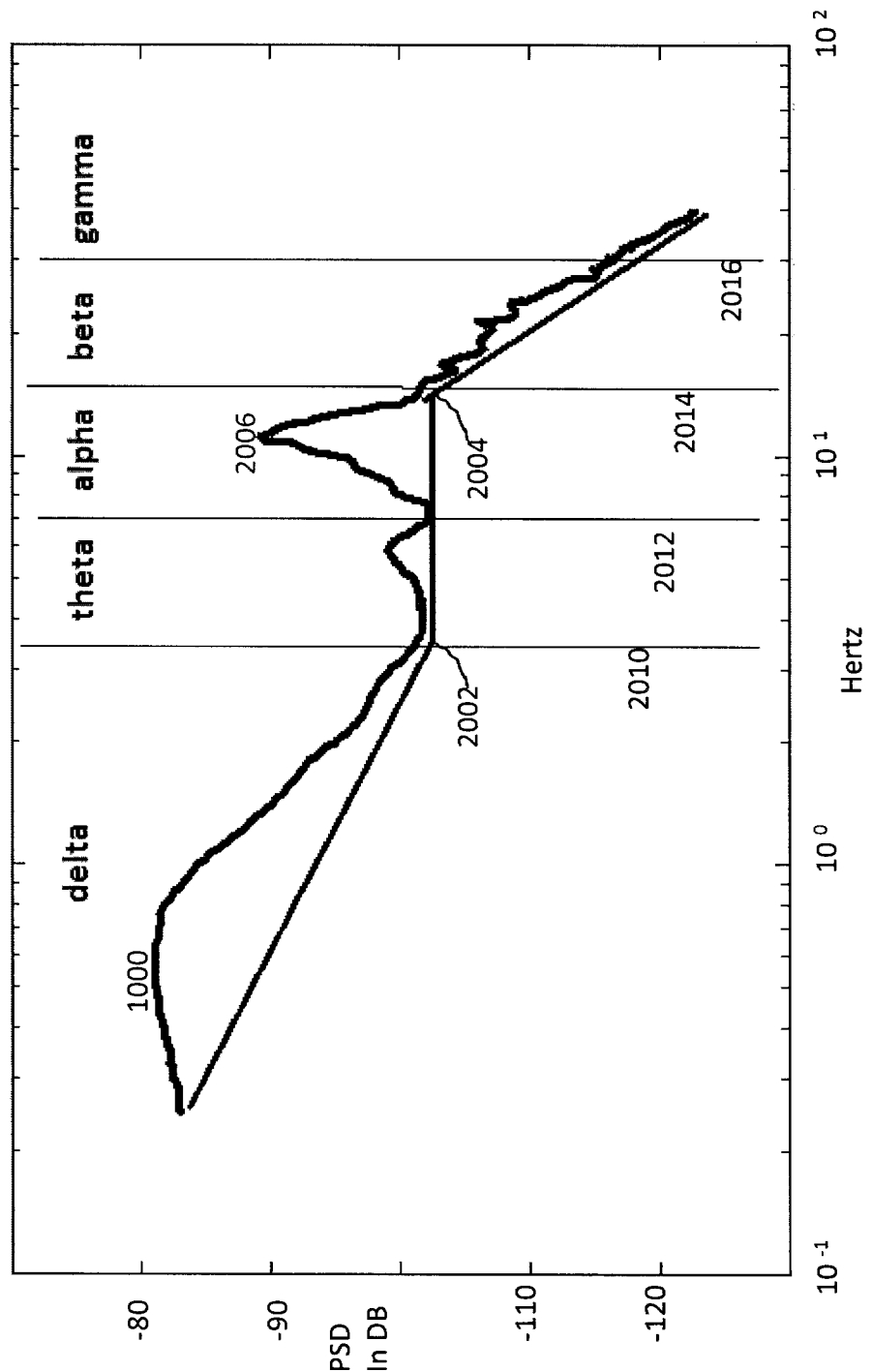
FIG. 2 illustrates the same spectrum with lines that indicate a version of the traditional frequency bands, delta (0-3.5 Hz), theta, (3.5-7 Hz), alpha (7-14 Hz), beta (14 30 Hz), and gamma (30-47 Hz).
Figure 3:
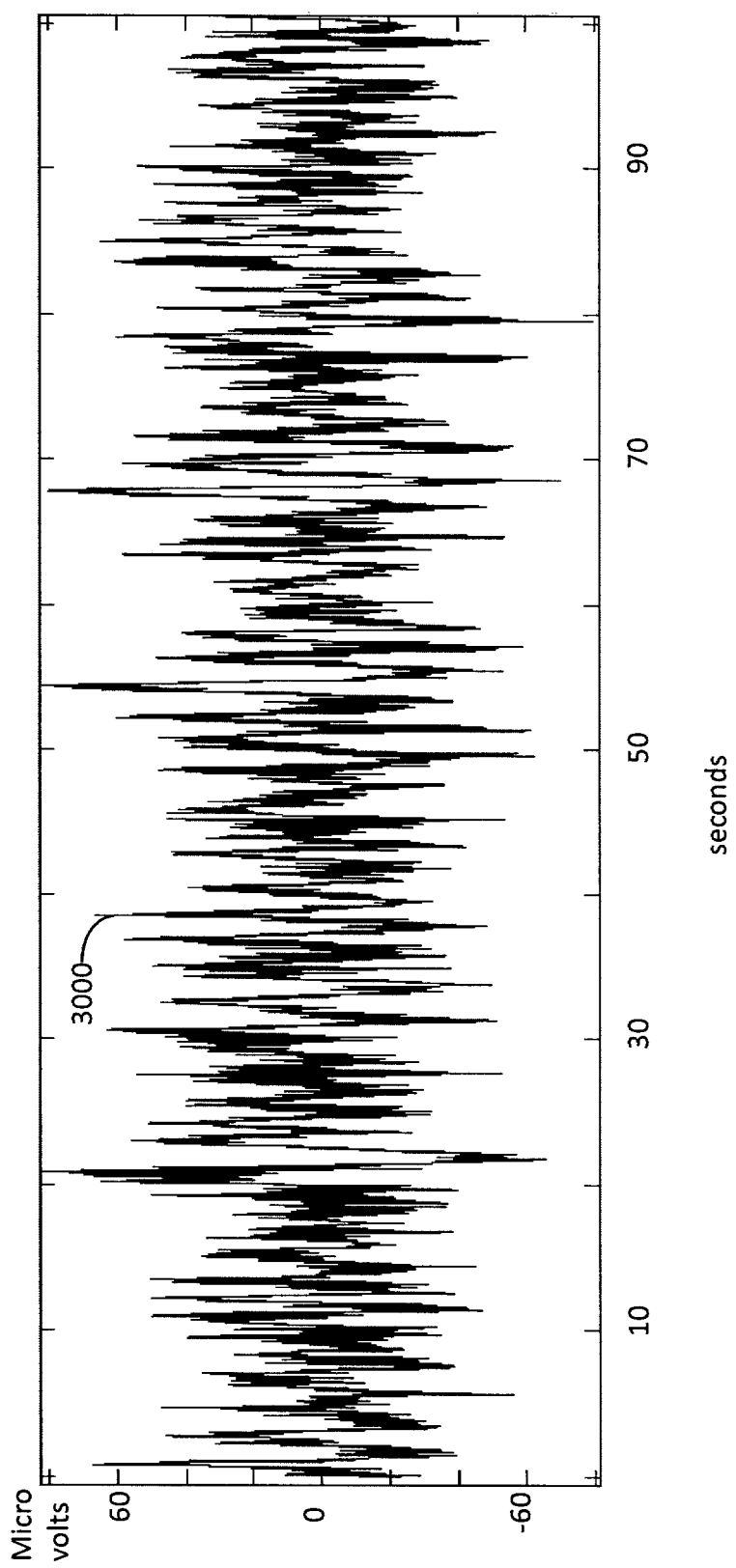
FIG. 3 illustrates the raw EEG signal that produced the spectrum in FIGS. 1 and 2.
Figure 4:
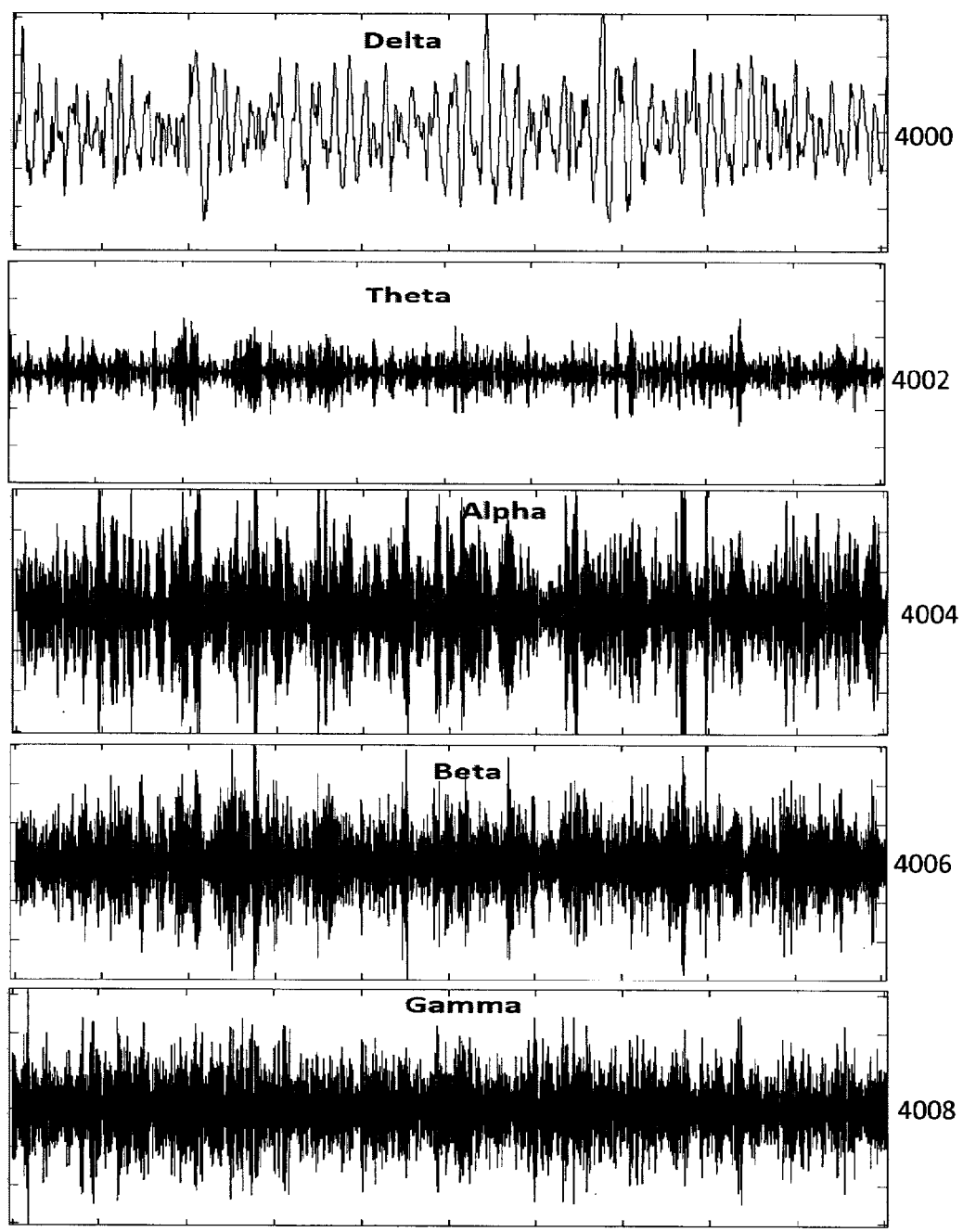
FIG. 4 illustrates the same EEG signal split into the 5 bands.

FIG. 1 is a log-log spectrum 1000 of the EEG of a patient that is at an adequate level of anesthesia. The spectrum 1000, in FIG. 1 is also approximated using three (for example) best fit lines 1002, 1003, 1004 using techniques described in the above-mentioned, incorporated patents and patent applications. FIG. 2 is the same spectrum 1000 with lines 2010, 2012, 2014, 2016 that indicate a version of the traditional frequency bands, delta (0-3.5 Hz), theta, (3.5-7 Hz), alpha (7-14 Hz), beta (14 30 Hz), and gamma (30-47 Hz). While these labels for the frequency bands are traditional, various features of the spectrum 1000 could also be used to identify a demarcation between the different bands such as, for example, the "delta band" and the "theta band". As such intersection points 2002, 2004 between two best-fit lines could be used to define a band's frequency range and the location of the alpha peak 2006 could also be used in defining one or more of the frequency bands of interest. It takes 30-60 seconds of EEG signal to produce a stable spectrum 1000 as shown in FIGS. 1 and 2. The spectrum 1000 can be monitored for sudden changes by separating the raw EEG signal into the separate bands with filters and displaying the separate frequency bands. FIG. 3 is the raw EEG signal 3000 that produced the spectrum 1000 in FIGS. 1 and 2. FIG. 4 is the same EEG signal split into the 5 bands (4000, 4002, 4004, 4006, 4008). In FIG. 4, because the amplitude of each band is different, the scale of the display can be adjusted in order to show the dynamic range of each band.

Figure 5:
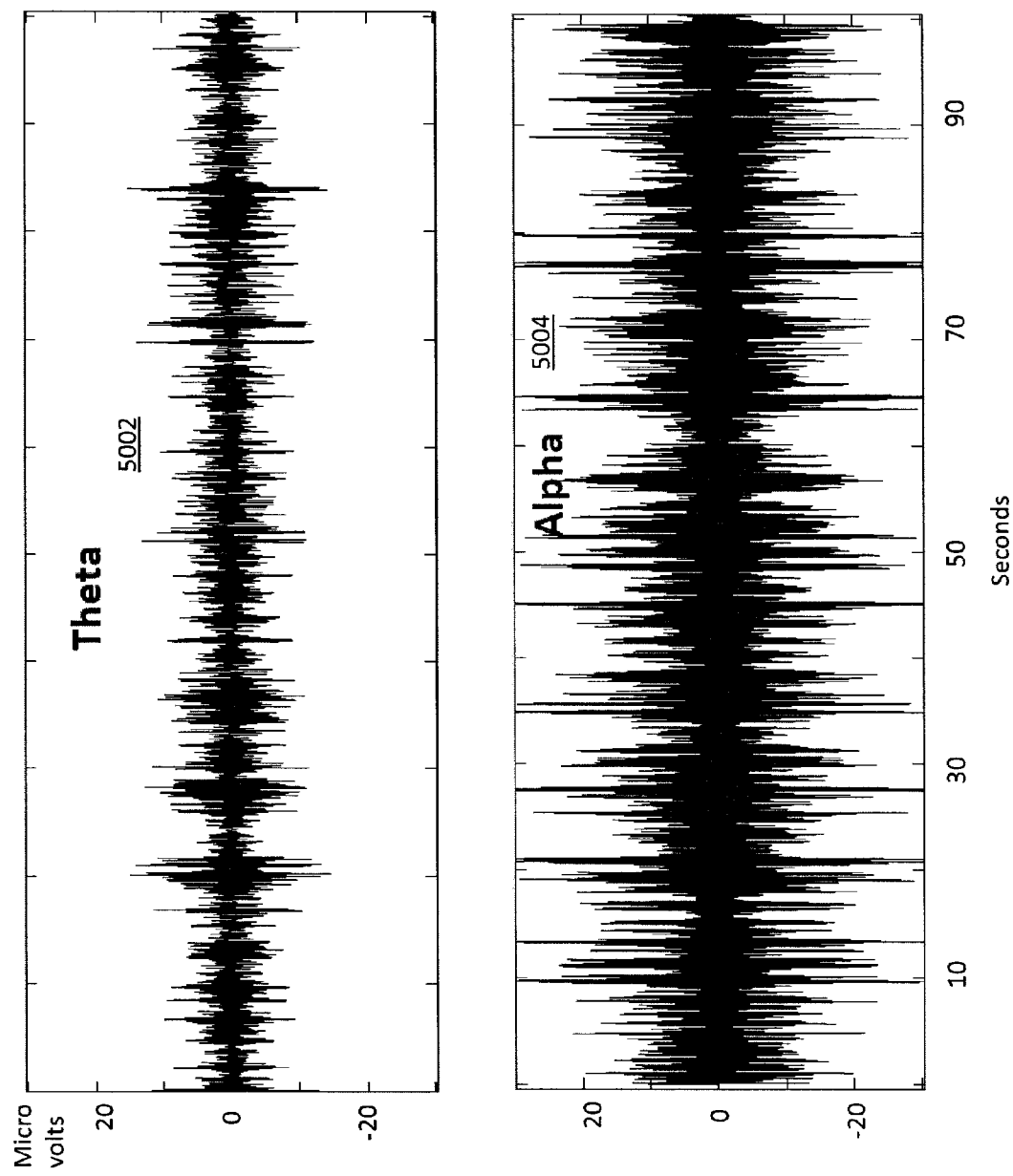
FIG. 5 illustrates the theta range and the alpha range on the same scale.
Figure 6:
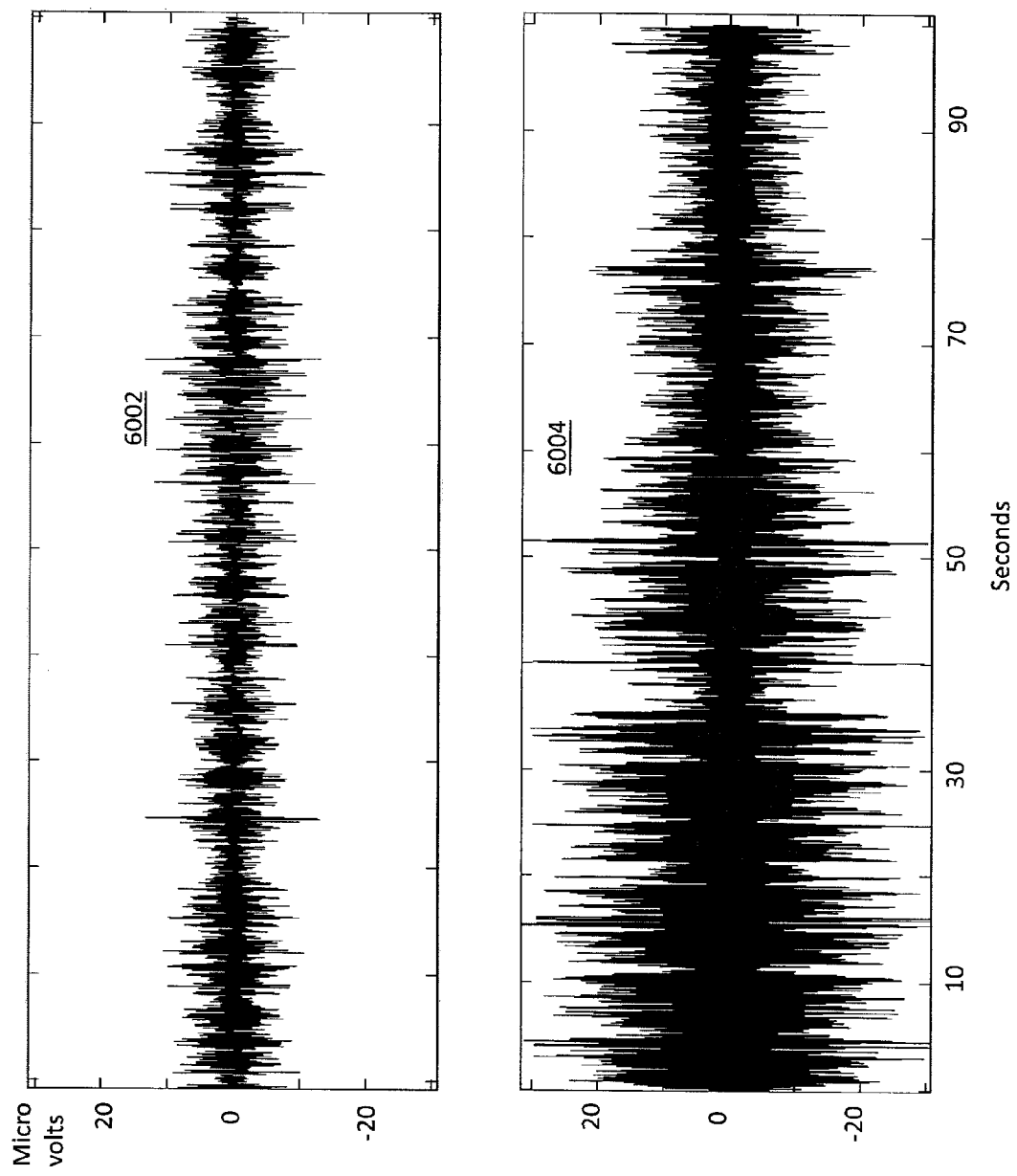
FIG. 6 illustrates a case in which the amplitude of the output of the digital filter for the alpha range became much less while the theta range did not change.
Figure 7:
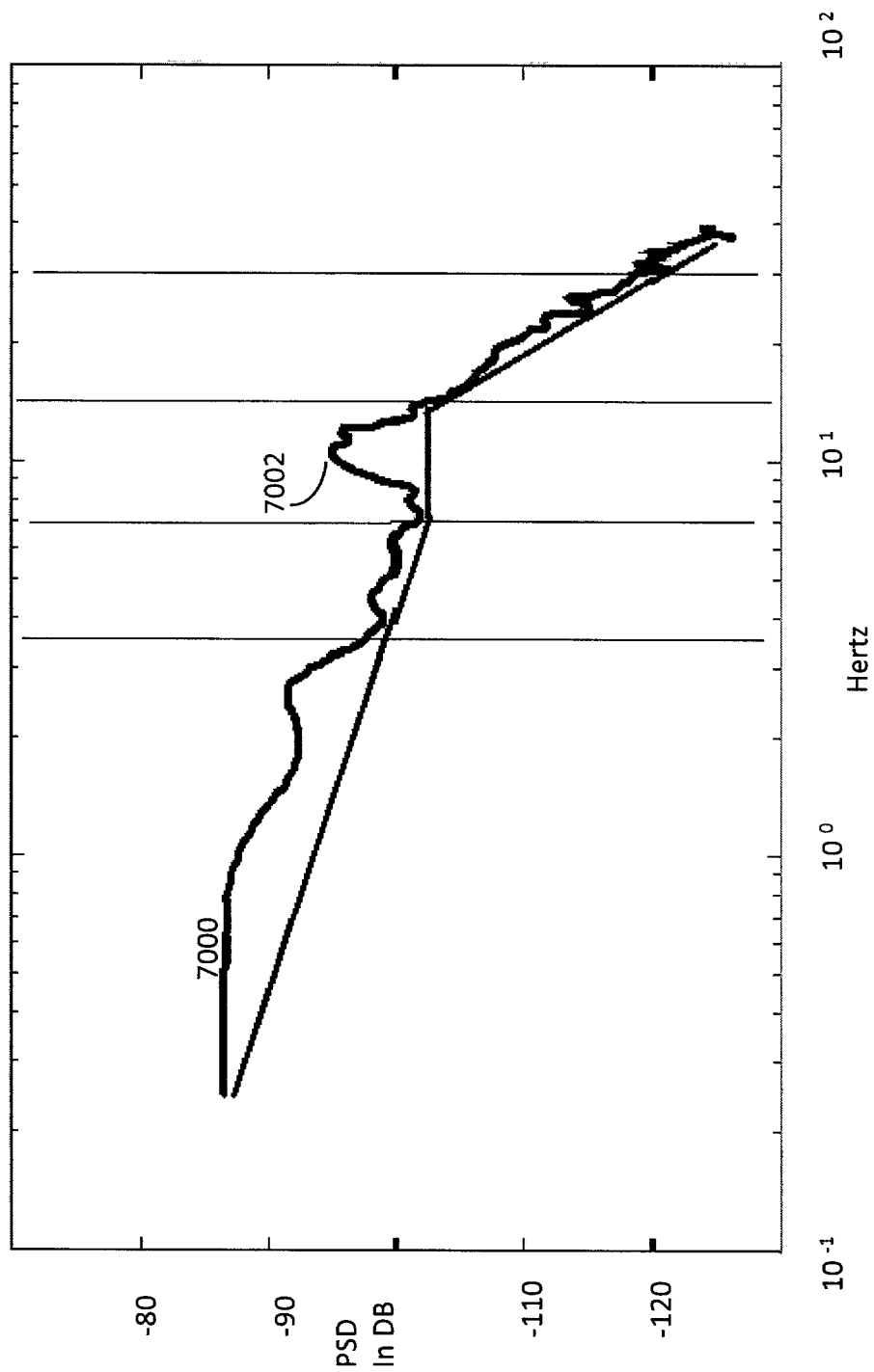
FIG. 7 illustrates the spectra for the period with the reduced alpha range amplitude.

In order to monitor the peak which occurs in the alpha range of the spectrum it is useful to monitor the output of a filter bank that splits the raw EEG signal into alpha and theta frequency ranges. In FIG. 5 the theta range 5002 and the alpha range 5004 are on the same scale (about ±30 microvolts). Since both bands are on the same scale the height of the alpha peak on the spectrum 1000 will be proportional to the amount the alpha band rises above the theta band in the output of the digital filter. In FIG. 5 it is apparent that there is much more amplitude in the alpha band 5004 than the theta band 5002 which is consistent with the large peak 2006 seen in the corresponding spectrum 1000 in FIG. 2. FIG. 6 shows that later during the surgery the amplitude of the output of the digital filter for the alpha range 6004 became much less while the theta range 6002 did not change (as compared to FIG. 5). FIG. 7 is the spectra 7000 for the period with the reduced alpha range amplitude (i.e., FIG. 6, 6004). It is apparent that the alpha peak 7002 is smaller in FIG. 7 than the alpha peak 2006 in FIG. 2. The advantage of monitoring the filtered bands is that a sudden change is immediately apparent in the time domain but the spectrum requires 30 to 60 seconds to show the change.

Figure 8:
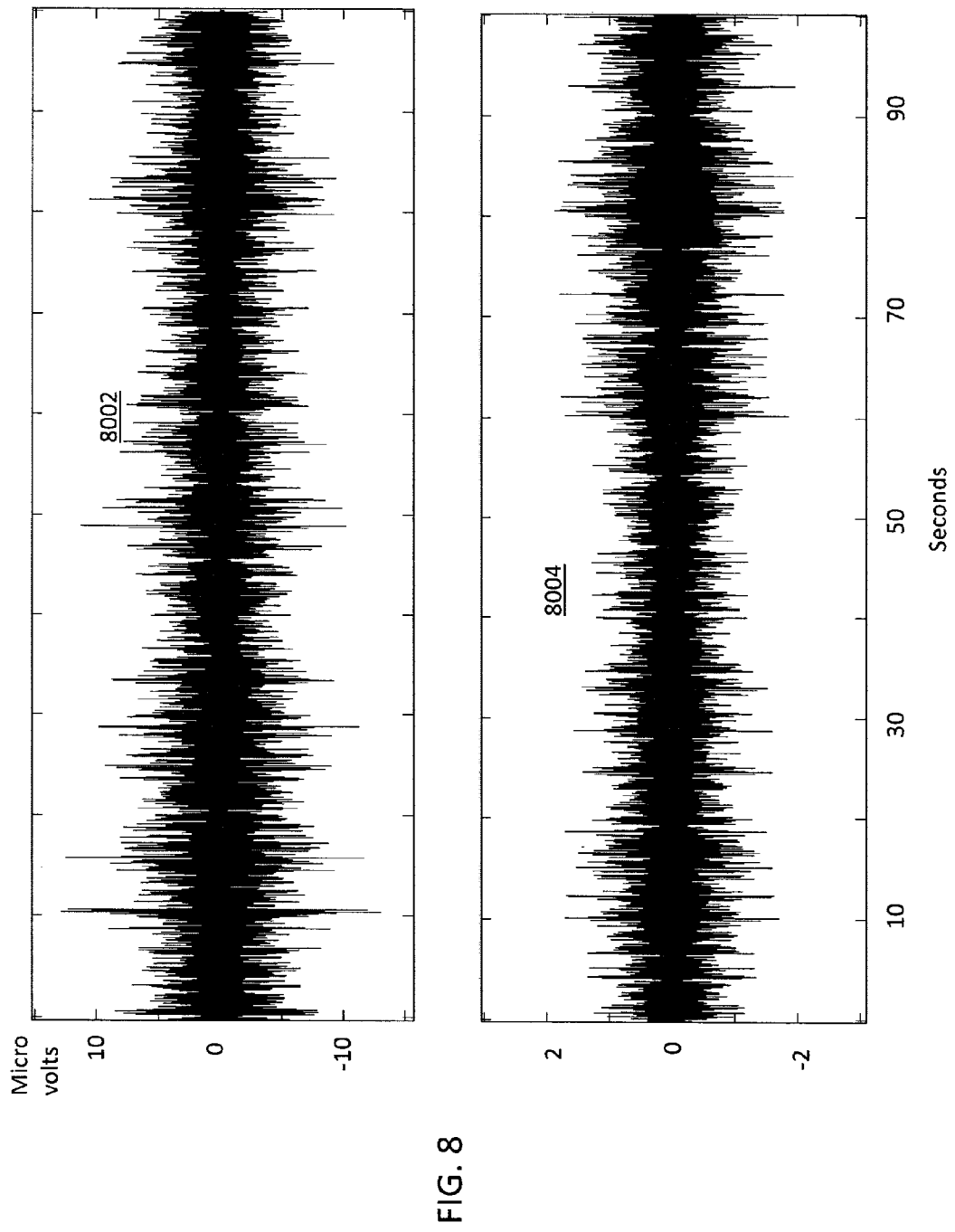
FIG. 8 illustrates a comparison of the beta band to the gamma band.

It is also useful to track the slope of the line that is in the beta and gamma ranges. To do this with filtered bands, the beta band can be compared to the gamma band. However, it is beneficial when doing so to make the scale on the gamma band different from the beta scale so that if the slope of the line is in the desired range they would appear to be equal. A ratio (of the scales) of five to one such as beta ranging from zero to fifteen and gamma ranging from zero to three (See filter outputs 8002, 8004 respectively in FIG. 8) will make both bands appear equal if the slope of the line (e.g., approximation line 1004 of FIG. 1) is as steep as commonly occurs during adequate anesthesia. On that scale a shallower slope would appear as higher amplitude in the gamma band relative to the beta band.

Figure 17:
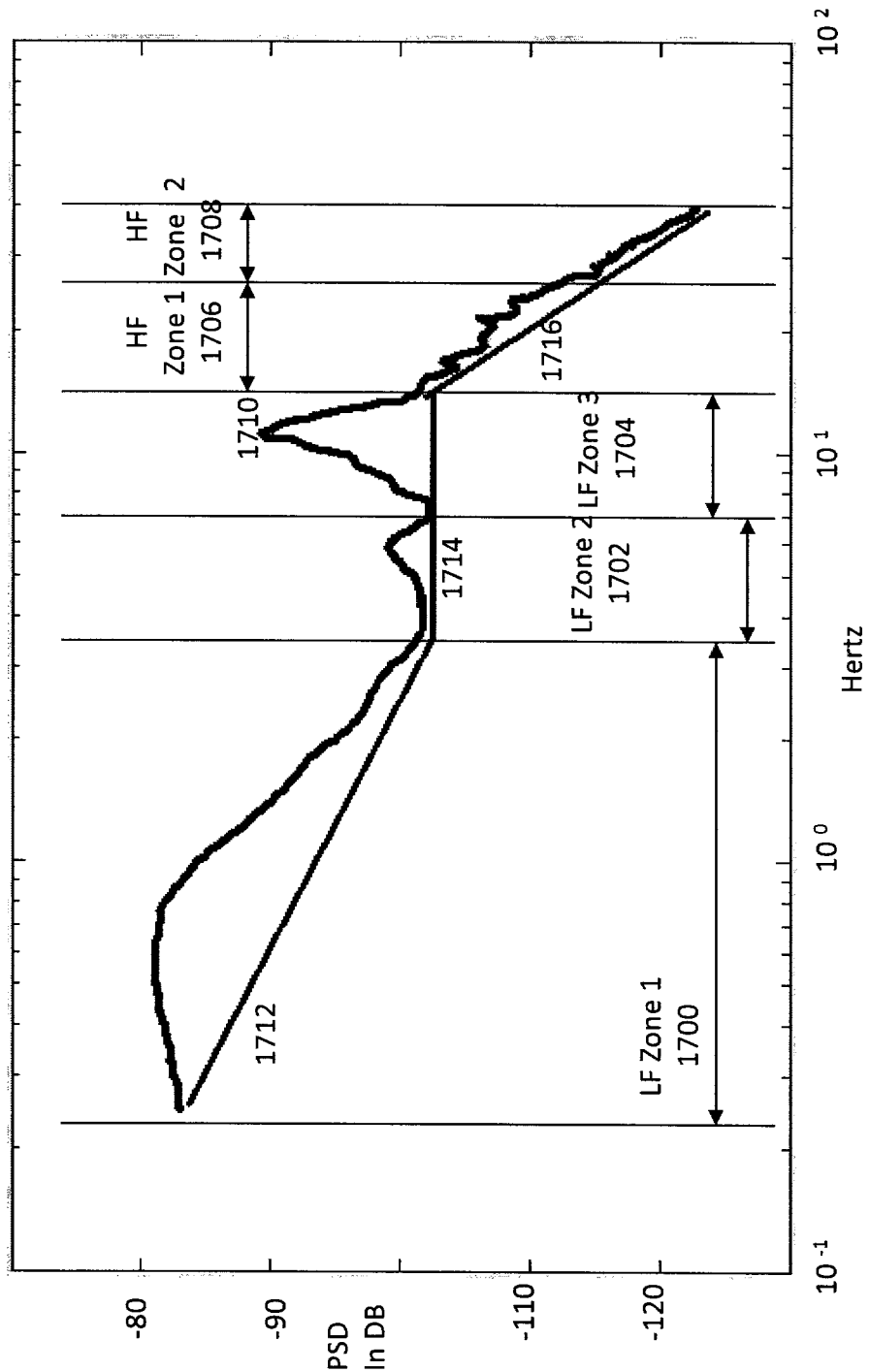
FIG. 17 illustrates the frequency bands of interest, as in FIG. 2, but are shown as more general bands.

As mentioned above, embodiments of the present invention are not limited to the conventional frequency bands associated with EEG technology. The frequency bands of interest are shown as more general bands in FIG. 17. The terms "alpha" and "theta" can mean the ranges where the peak and the trough occur respectively. The term "beta" can refer to starting a band at a point where the straight line that we refer to as the HF (high frequency) line begins which may be a higher frequency than the traditional definition of beta. The term "gamma" can refer to a range that is lower than the traditional definition of gamma in order to avoid the effects of facial muscle activity (EMG). Thus, as shown generally in FIG. 17, the filtering of time domain data can occur in more generically labeled frequency bands such as, low frequency zone one 1700, a low frequency zone two 1702, a low frequency zone three 1704, high frequency zone one 1706, and high frequency zone two 1708 and the ranges of these bands can vary based on characteristics of a particular EEG spectrum 1710 and its best-fit approximation lines 1712, 1714, 1716.

Figure 9:
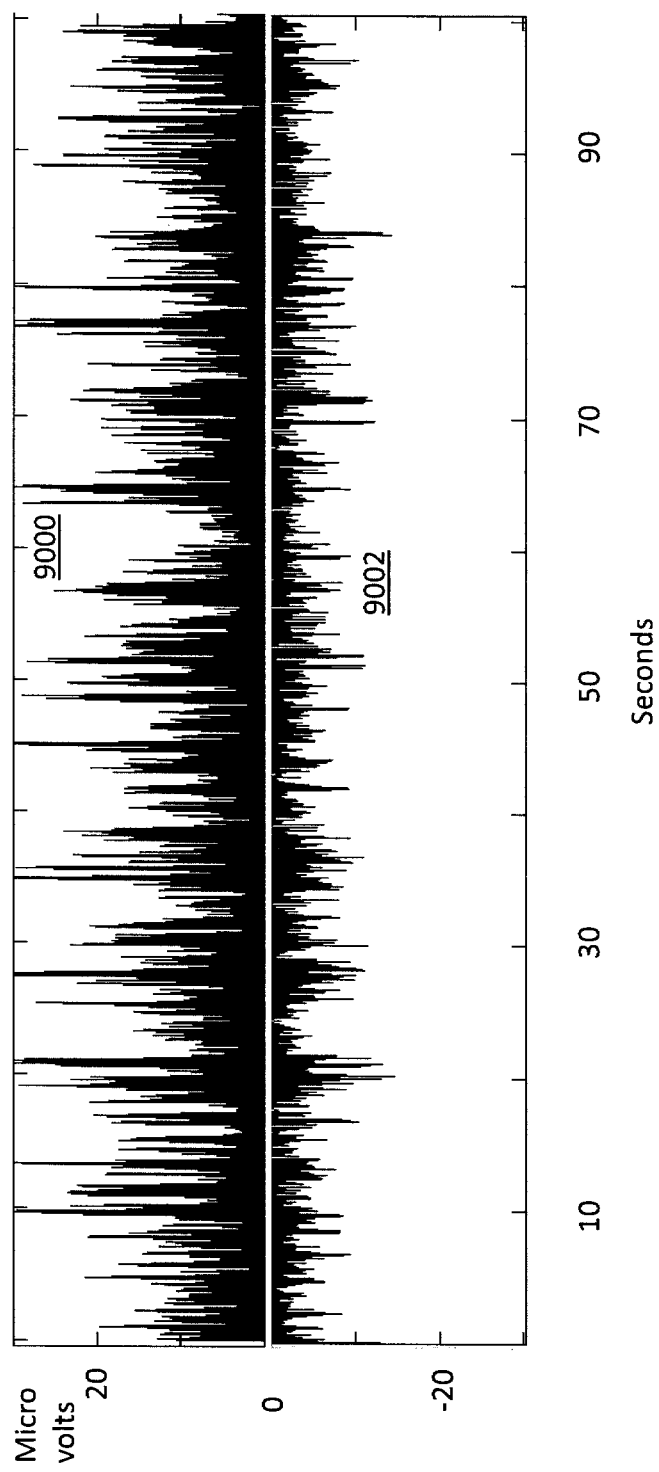
FIG. 9 illustrates the upper half of the alpha band and the lower half of the theta band from FIG. 5.
Figure 10:
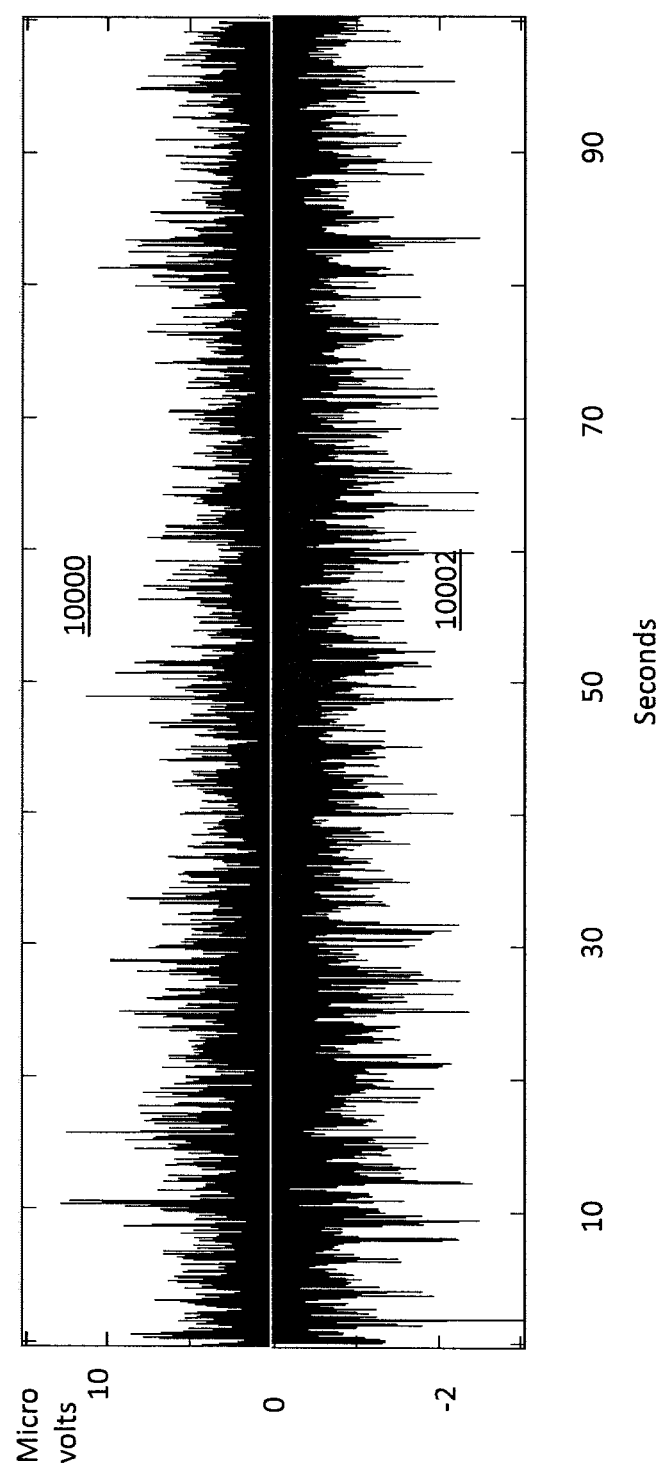
FIG. 10 illustrates the upper half of the beta band (±15 micro volts) and the lower half of the gamma band (±3 micro volts) from FIG. 8.

Since the filtered bands are largely symmetrical above and below the zero value the positive half of one band can be displayed above the negative half of another band to show the amplitude of one band relative to another band. FIG. 9, for example, shows the upper half of the alpha band 9000 and the lower half of the theta band 9002 from FIG. 5. FIG. 10 shows the upper half 10000 of the beta band (±15 micro volts) and the lower half 10002 of the gamma band (±3 micro volts) from FIG. 8. One of ordinary skill will recognize that different pairs of bands can be displayed in this manner (e.g., alpha and beta rather than alpha and theta) and different relative scaling can be selected without departing from the scope of the present invention. However, the example values of FIG. 9 and FIG. 10 are particularly beneficial in visually conveying almost immediate changes occurring in an EEG signal.

Figure 11:
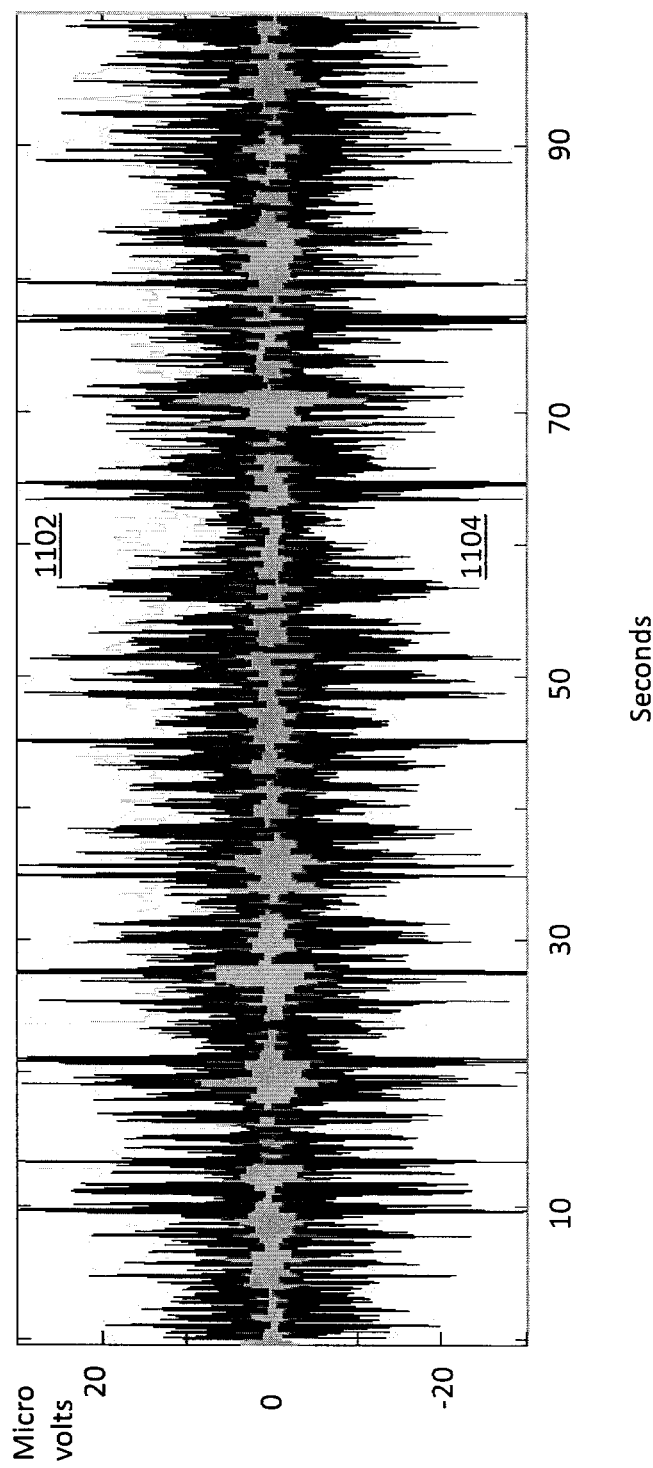
FIG. 11 illustrates the theta band from FIG. 5 (grey) superimposed on the alpha band from FIG. 5 (black).
Figure 12:
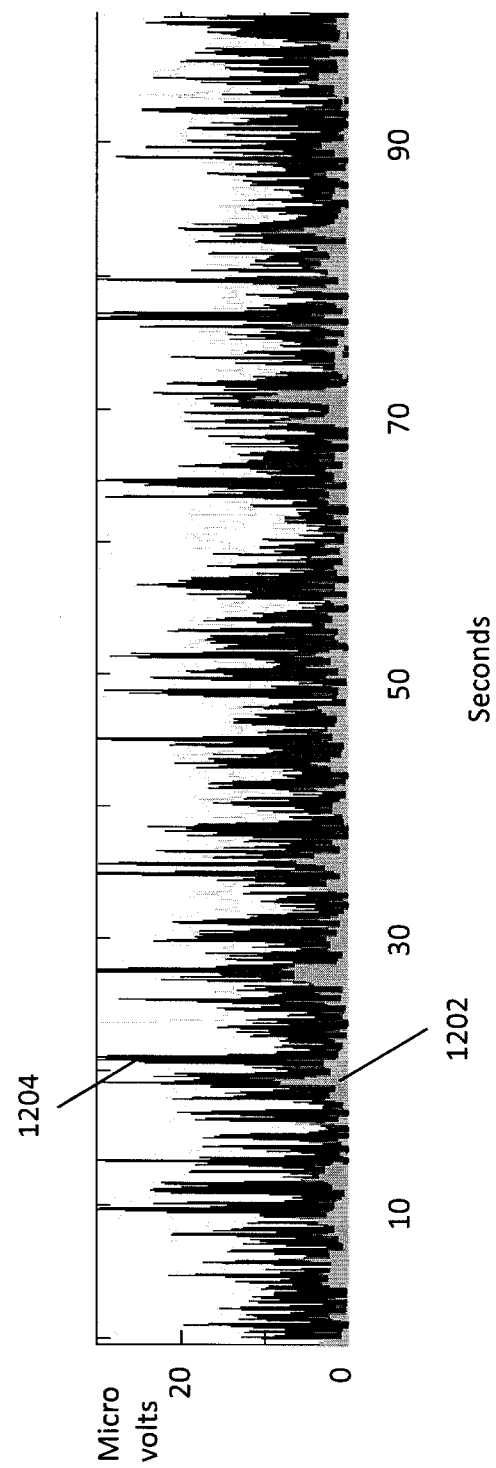
FIG. 12 illustrates that only half of FIG. 11 provides similar information.
Figure 13:
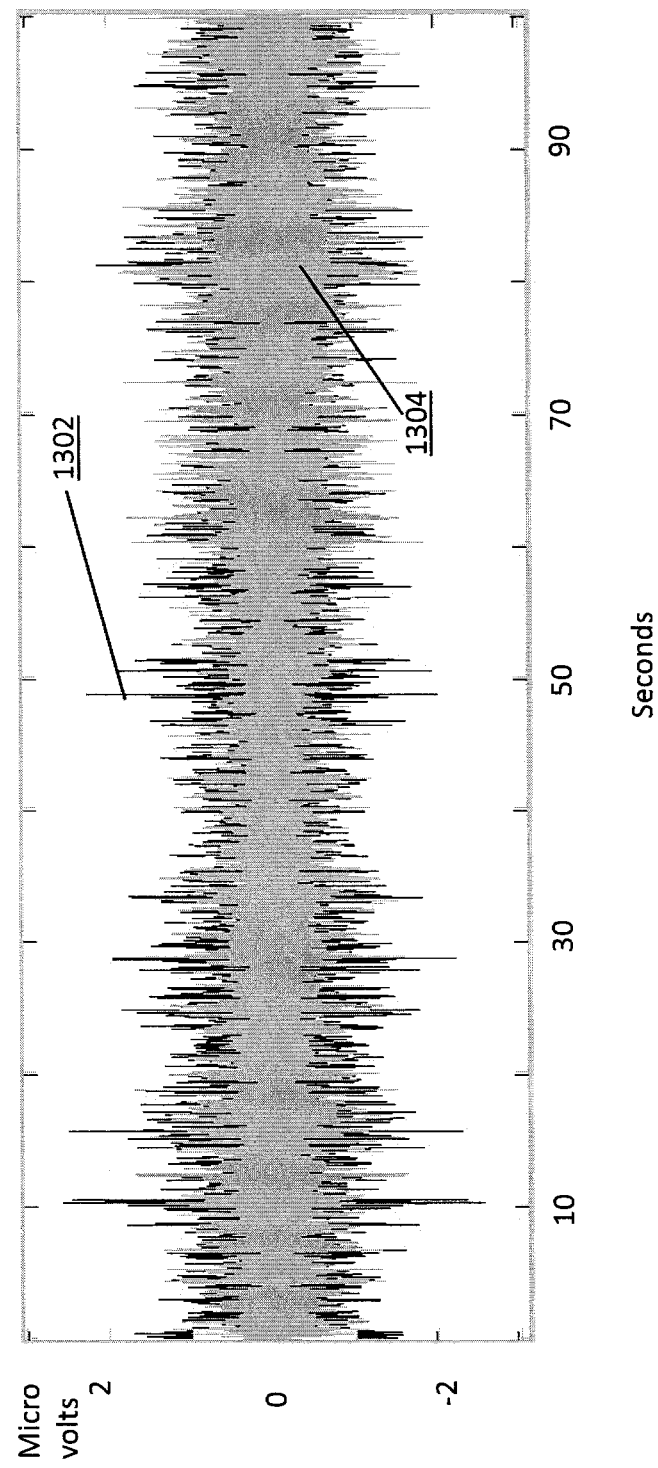
FIG. 13 illustrates the beta band from FIG. 8 (grey) superimposed on the gamma band (black) from FIG. 8.

Another way to facilitate comparing two bands while saving space is to superimpose one band on another band utilizing two different colors or grey on black. The term "superimposing" does not merely mean that two or more different bands are displayed in a display area but that the two, or more, bands at least partially overlap in a spatial manner within that display area. Thus, the terms "superimpose", "overlap", or "overlaid" may be used interchangeably within the present description. FIG. 11 shows the theta band 1102 from FIG. 5 (grey) superimposed, or overlaid, on the alpha band 1104 from FIG. 5 (black). Furthermore, FIG. 12 illustrates that using only half of FIG. 11 can visually convey essentially the same information about the alpha band 1204 relative to the theta band 1202. FIG. 13 illustrates the beta band 1302 from FIG. 8 (grey) superimposed, or overlaid, on the gamma band 1304 (black) from FIG. 8. As in FIG. 8 the scale of the two bands is five to one so that if the slope of the line through the beta and gamma zones is appropriate the two bands will appear of substantially equal size.

Figure 14:
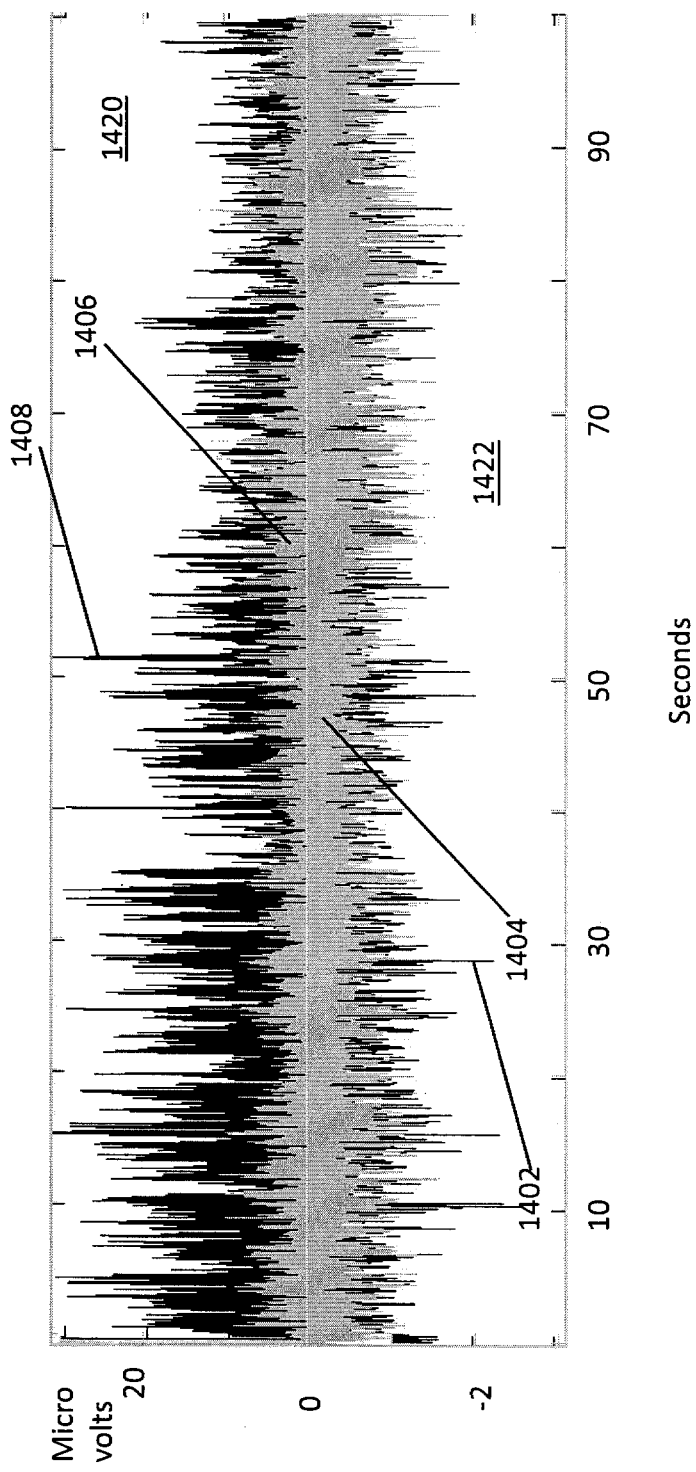
FIG. 14 illustrates superimposing the upper half of one band on the upper half of a second band and the lower half of a third band on the lower half of a fourth band.

A further improvement would superimpose the upper half of one band 1406 on the upper half of a second band 1408 and the lower half of a third band 1402 on the lower half of a fourth band 1404, as shown in FIG. 14. This would not only compress the information from 4 bands into the space of one band but would also make it much easier to compare their relative amplitudes and appreciate in near real time any changes in their absolute and relative amplitudes. Using the example of FIG. 14, a user can evaluate the size of the alpha peak 1408 relative to the theta band 1406 with an upper half 1420 of the display and a slope of the spectrum in the beta 1402 and gamma 1404 region with a lower half 1422 of the display. FIG. 7 is the EEG spectrum 7000 generated from the EEG signal during the last half of FIG. 14. The alpha peak 7002 is reduced and there is no change in the slope of the beta and gamma region.

Figure 15:
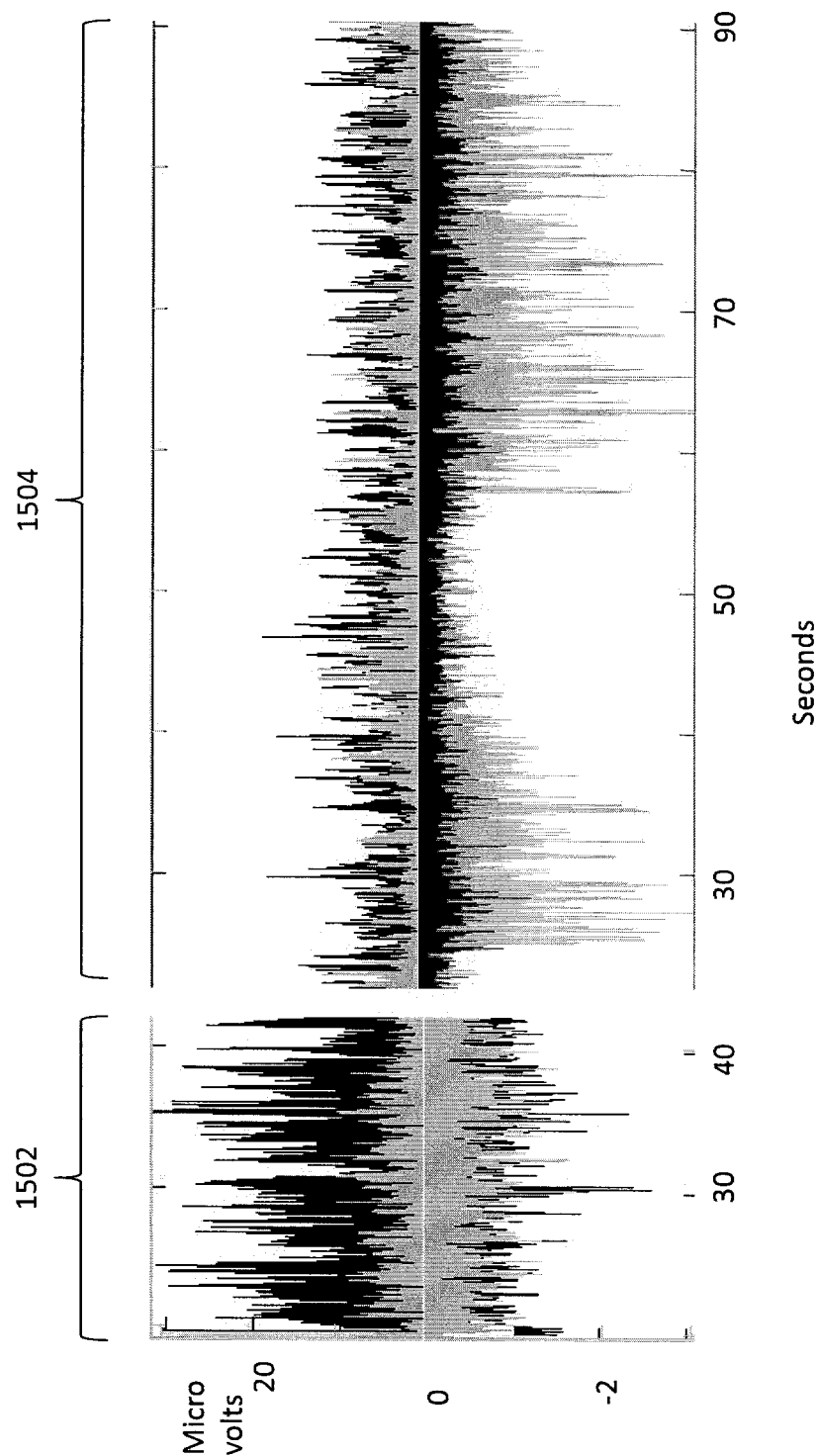
FIG. 15 illustrates a much reduced alpha peak and increased activity in the gamma range.
Figure 16:
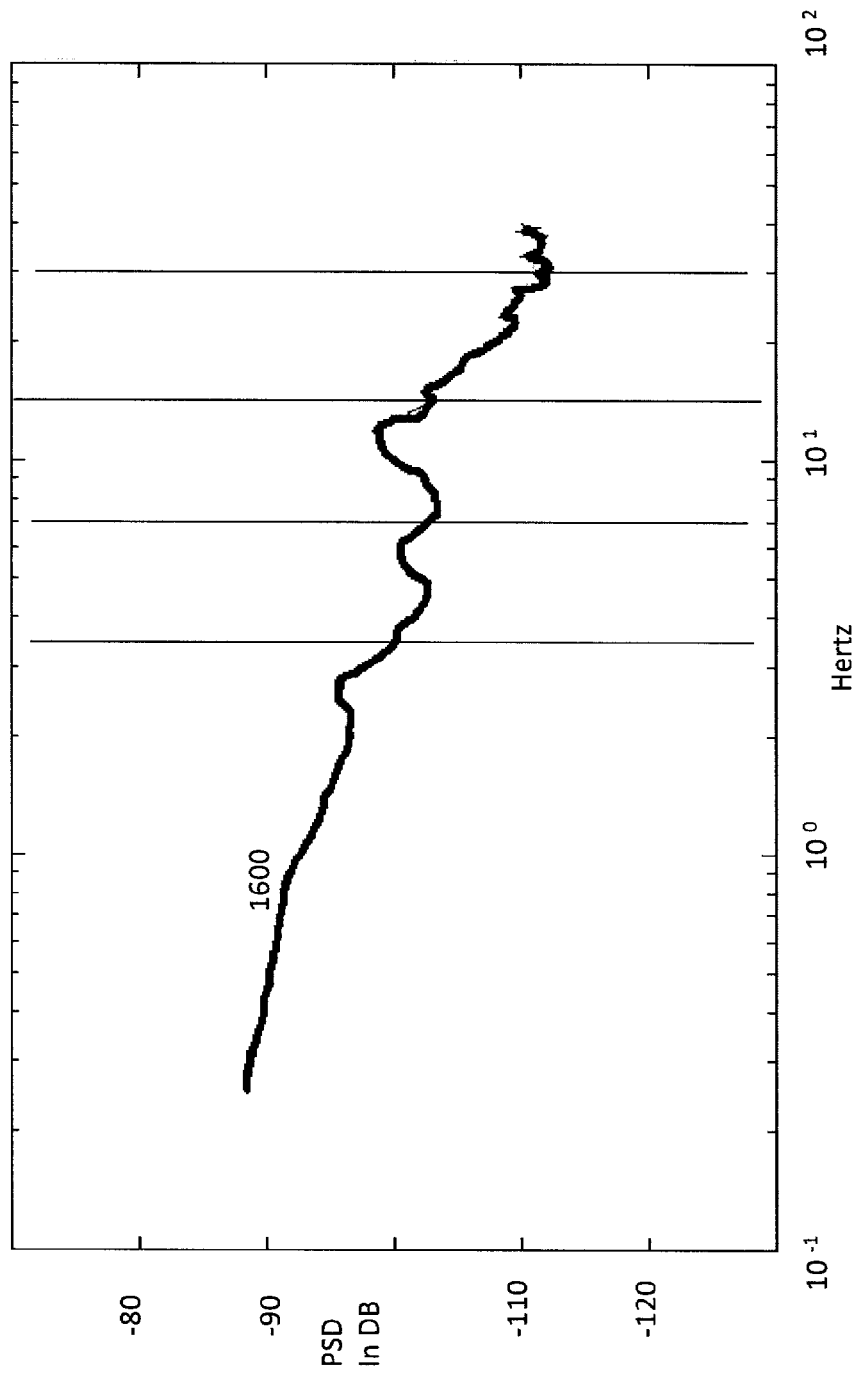
FIG. 16 illustrates a spectrum of the EEG signal from the later part of FIG. 15.

It may be beneficial to save and display for reference a section 1502 of the multiple filtered bands from an earlier time in a surgical procedure along with the current output 1504 of the multiple filters as illustrated in FIG. 15. FIG. 15 shows that in the current output 1504 there is a much reduced alpha peak and increased activity in the gamma range. In fact, as between the reference output 1502 and the current output 1504, the increase in gamma is so much that the color scheme (e.g., gray for beta and black for gamma) had to be reversed or the gamma band would have completely obscured the beta activity. As one alternative to changing color schemes in this manner, the display for each band that is overlaid on another can use some varying degree of transparency, or opacity, so as not to obscure the band it overlays. For reference, the EEG signal from the later part of FIG. 15 generated the spectrum 1600 in FIG. 16.

On a conventional anesthesia monitor there is a lot of information of multiple modalities on one screen and a display of the information discussed above on the screen with the electrocardiogram, respiration data, blood pressure and more would preferably be done in such a manner as to not crowd out other information. Thus, the example display graphs discussed above not only save space but make it easier to visualize changes. This can provide the benefit of a near real time update advantage of the time domain approach.

Another band of interest could include the lower frequency delta or an extended delta up to 6 Hertz (or the trough point on the EEG spectrum) which corresponds to something called the "slow wave". Comparing the wave to the spindle wave is useful in determining the effective level of anesthesia. This additional band may be shown with the alpha and theta bands superimposed on it. This would be three half bands superimposed.

Another band of interest can include the EMG band. Tracking changes in activity attributable to the facial muscles can help the anesthesia provider assess the level of analgesic or muscle relaxant agents. This band or half band could be superimposed on the beta and gamma bands. This would enable six bands to be tracked in a compact manner.

As mentioned above, different color schemes can be used to help all displayed bands be visible but, also, when bands or half bands are superimposed the top band can be either opaque or have some degree of transparency which would enable the user to visualize the band underneath if the top band has greater amplitude.

Adding horizontal reference lines may be beneficial to improve the ability to appreciate changes in amplitude. Adding vertical reference lines would provide a time reference. Also, the half-band signal described above may be provided on either a top half of a display or a bottom half of the display by providing a "mirror-image" of the signal in order to display properly.

Some conventional EEG technologies provide a graph of the RMS values of the traditional EEG bands but, in contrast, the techniques described above may use the actual filtered signal on the time scale of up to 30 seconds. Thus, this method described above is not to be confused with graphing the RMS value of the traditional bands. When this is done it is usually done with either bar graphs or a stacked area graph. Superimposing one band on another is not the same as stacking one value on another in a graph. Superimposing has the same location for the zero value of all variables while stacking has the zero value for the second variable located at the maximum value for the first variable and so on for any subsequent variables. Also, the peaks and troughs that occur in frequency bands, as discussed herein, are very different than RMS values for those frequency bands. While delta peaks and alpha peaks may have previously been identified as being related to indicating awareness, embodiments of the present invention also recognize that the amplitude and frequency of the theta trough that occurs between them is an important indicator as well.

In the techniques described above selection is made of a short time scale to show changes in near real time while monitoring (not reviewing). This short time scale is able to show individual cycles in the oscillations. An intermediate time scale is able to show packets (or "bursts") of oscillations. And a long time scale shows trends over a longer time period. These different scales are not to be confused with "superimposed" that involves a stacked area, stacked bar, or side by side bar graph in the scale of trend such as 5 minutes or longer.

Packets can identify burst suppression. By appropriate adjustment of different timescales identification can occur of this phenomenon of bursts in different frequency bands starting and stopping simultaneously instead of starting and stopping at different times. When they are observed to start and stop simultaneously, this is an indication of bursts of pink noise which is typical of burst suppression. Bursts at different frequencies starting and stopping at different times imply that there are multiple oscillation generators functioning independently. This is typical of an EEG pattern that occurs at a lower level of anesthesia than burst suppression.

The techniques and methods described above can be generally summarized as including:

1) Using the upper half or the lower half of a filtered band. Displaying two such half bands with either the upper half of one above the lower half of another or one upper (lower) superimposed on another upper (lower). A third half band could be superimposed.

2) Selecting frequency ranges for the half bands to indicate the size of a peak in the spectrum (alpha and theta).

3) Selecting and adjusting the scale of two bands such that comparing them for amplitude will indicate the slope of a section of the spectrum.

In certain embodiments of the present invention it may be beneficial to combine the 0.1-1 Hz with the 7-14 Hz Bands. Some research suggests that if most of the 7-14 Hz activity occurs at the trough of the 0.1-1 Hz wave ("trough max") the patient is close to waking up; and if most of the 7-14 Hz activity occurs at the peak of the 0.1-1 Hz wave ("peak max") the patient is at a deep level of anesthesia. Another phenomena known as the "Cortical slow wave" or "slow wave" can occur at a frequency as high as about 6 Hz or to the theta trough. Thus, combining a signal with a band of frequencies from about 0.1 to 6 Hz with another signal with a band of frequencies from about 7-14 Hz is also contemplated within the scope of the present invention.

As mentioned above, providing a display which superimposes, or overlays, different bands of a monitored EEG signal may make it easier to visualize the relationship between the two bands. One additional alternative is that of combining, or mixing, the two bands into a single trace to generate an "improved" raw EEG signal. The user could click some type of input device and toggle back and forth between displaying a raw signal and a signal that combines 0.1-1 Hz with 7-14 Hz (for example) in one trace. One of ordinary skill will recognize mixer circuitry for combining two or more signals can be designed and configured in a variety of different ways without departing from the scope of the present invention.

FIGS. 23-26 illustrate various examples of combined, or mixed, signals and displaying them in accordance with the principles of the present invention. FIG. 27 depicts an exemplary apparatus 2700 for combining two bands of an EEG signal. A time-domain EEG signal 2702 is acquired and separated into three paths 2704, 2705, 2707. The path 2704 is an unadulterated version of the EEG signal 2702. However, the signal path 2705 feeds a first bandpass filter 2706 that provides an output signal 2709 to a mixer 2710. The signal path 2707 feeds a second bandpass filter 2708 that provides its own output signal 2711 to the mixer 2710. At the mixer, the two output signals 2709, 2711 are combined to produce an "improved" EEG signal 2712. A user-controllable switch 2714 allows selection of either the EEG signal 2704 or the improved EEG signal 2712 as a signal 2716 that is provided for display to the user via the EEG display 2718.

Figure 23:
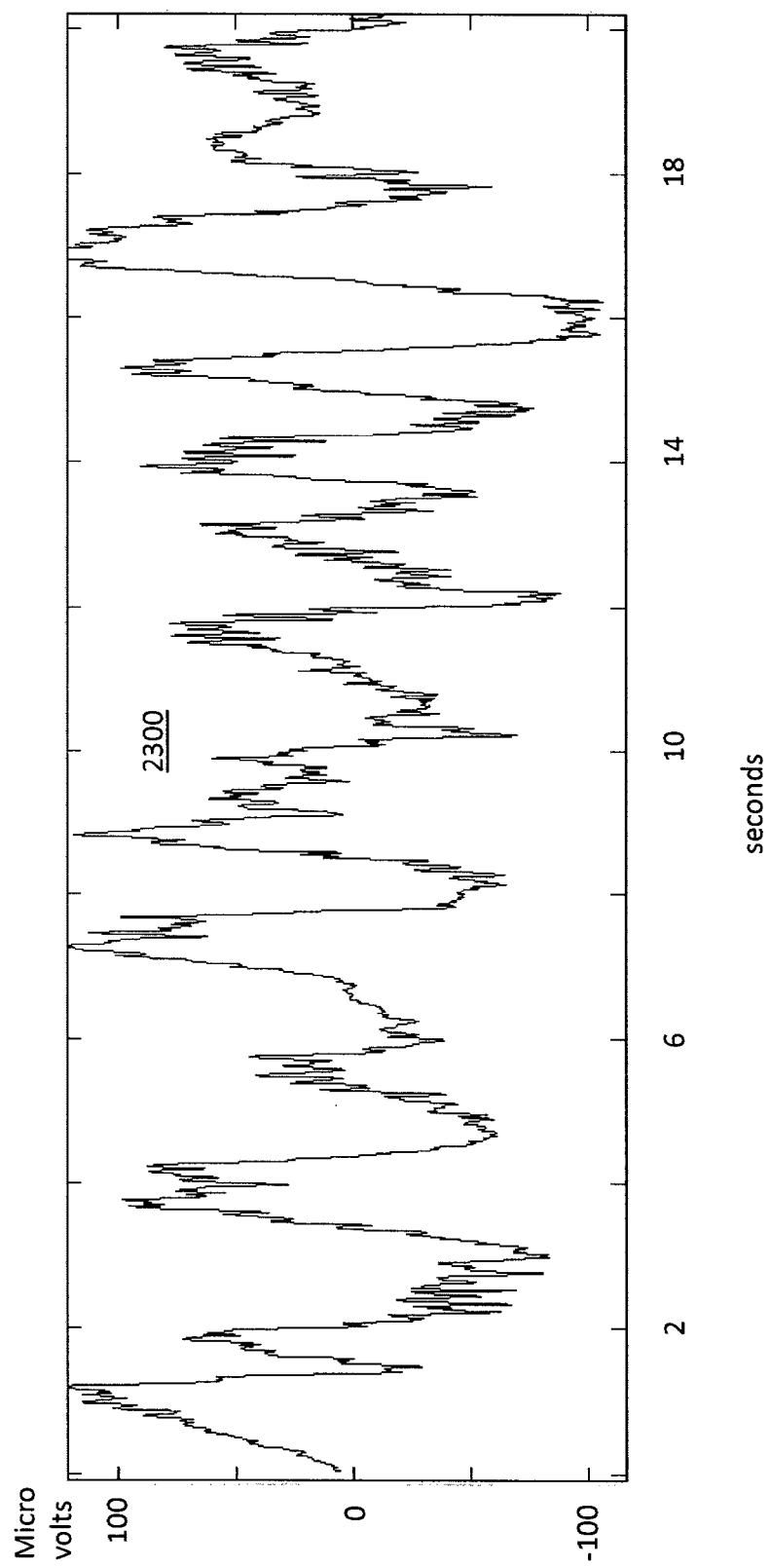
FIGS. 23-26 are a group of figures illustrating the individual signals useful for generating an example combined signal in accordance with the principles of the present invention.
Figure 24:
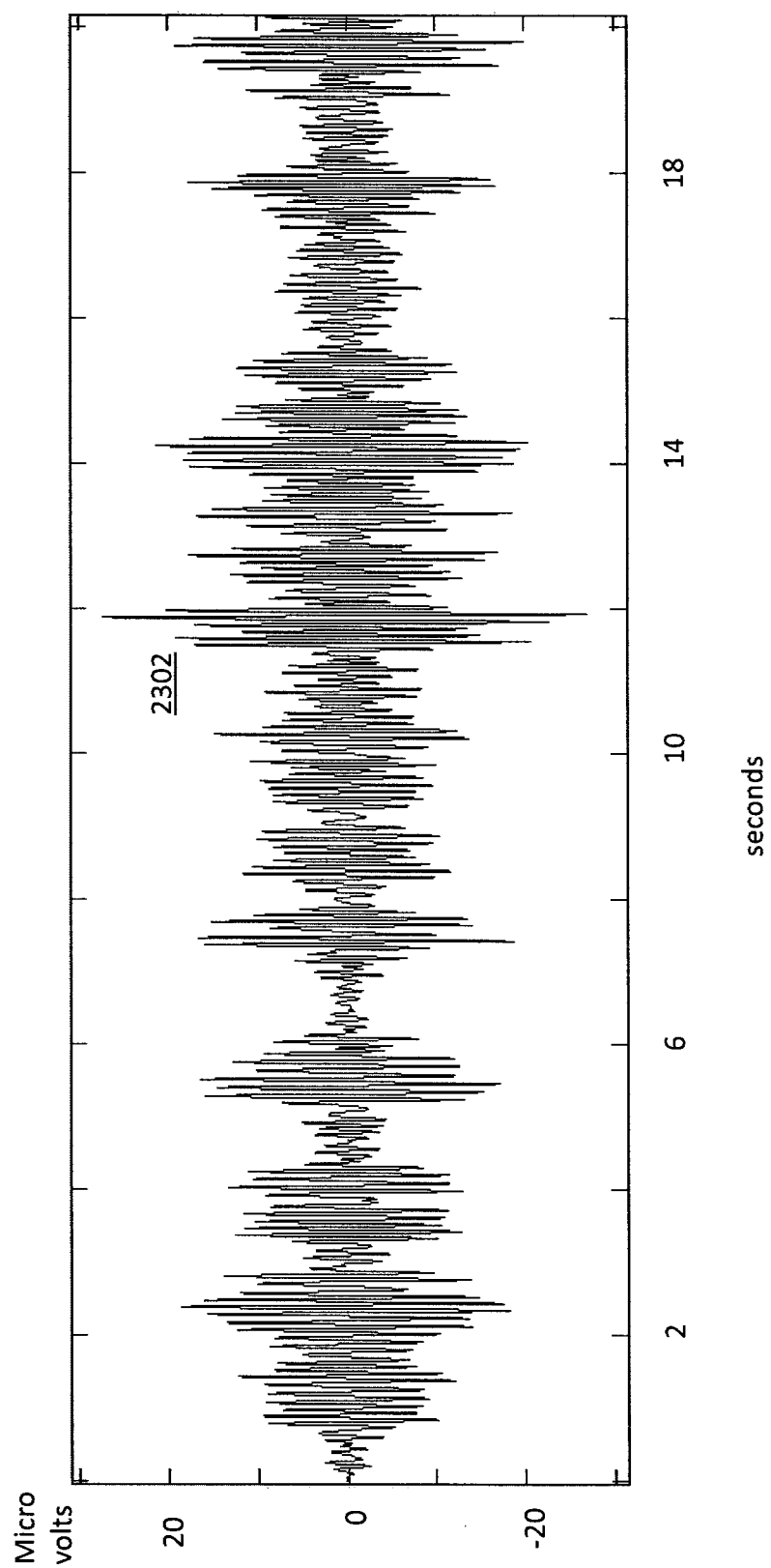
Figure 25:
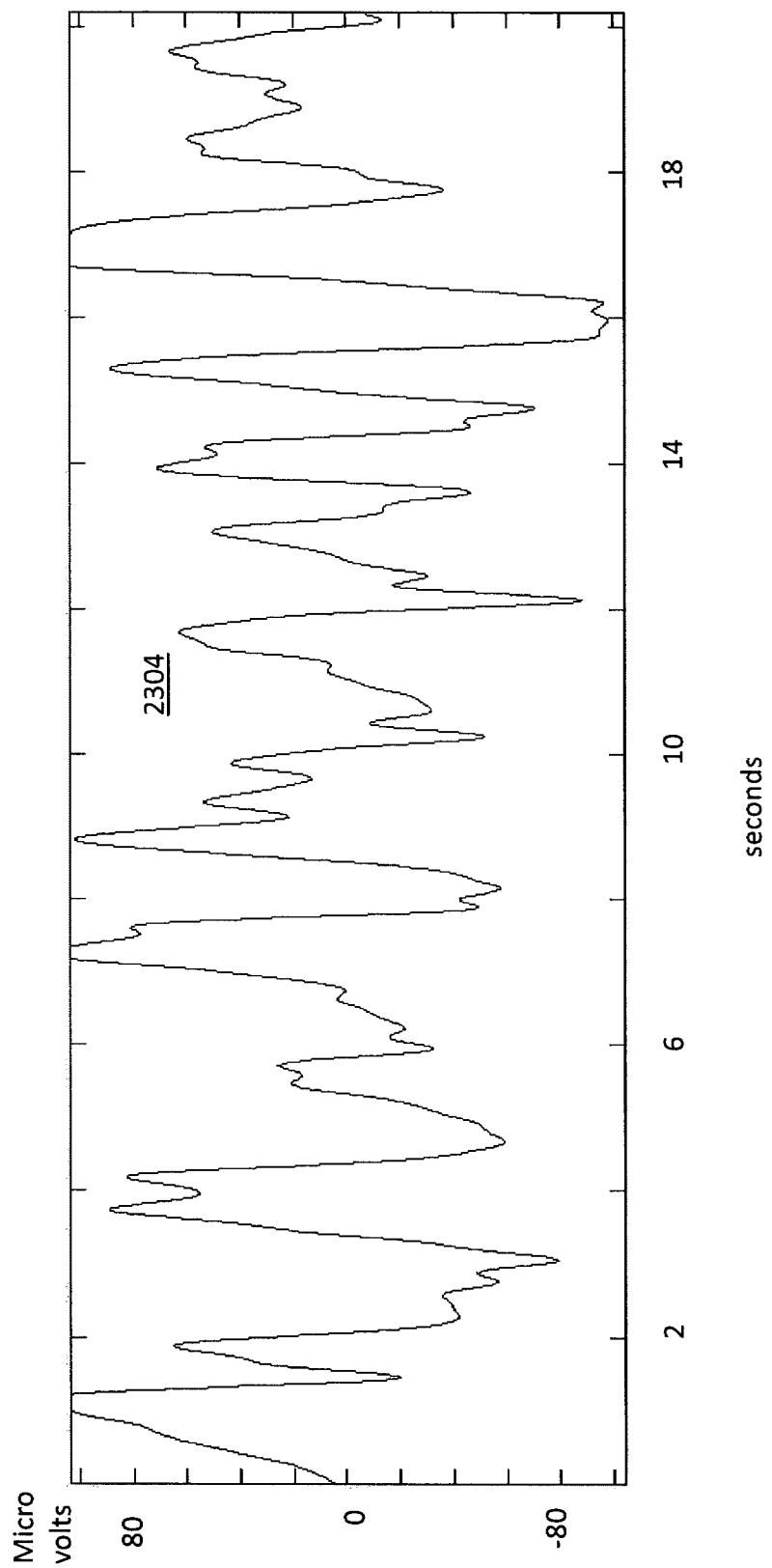
Figure 26:
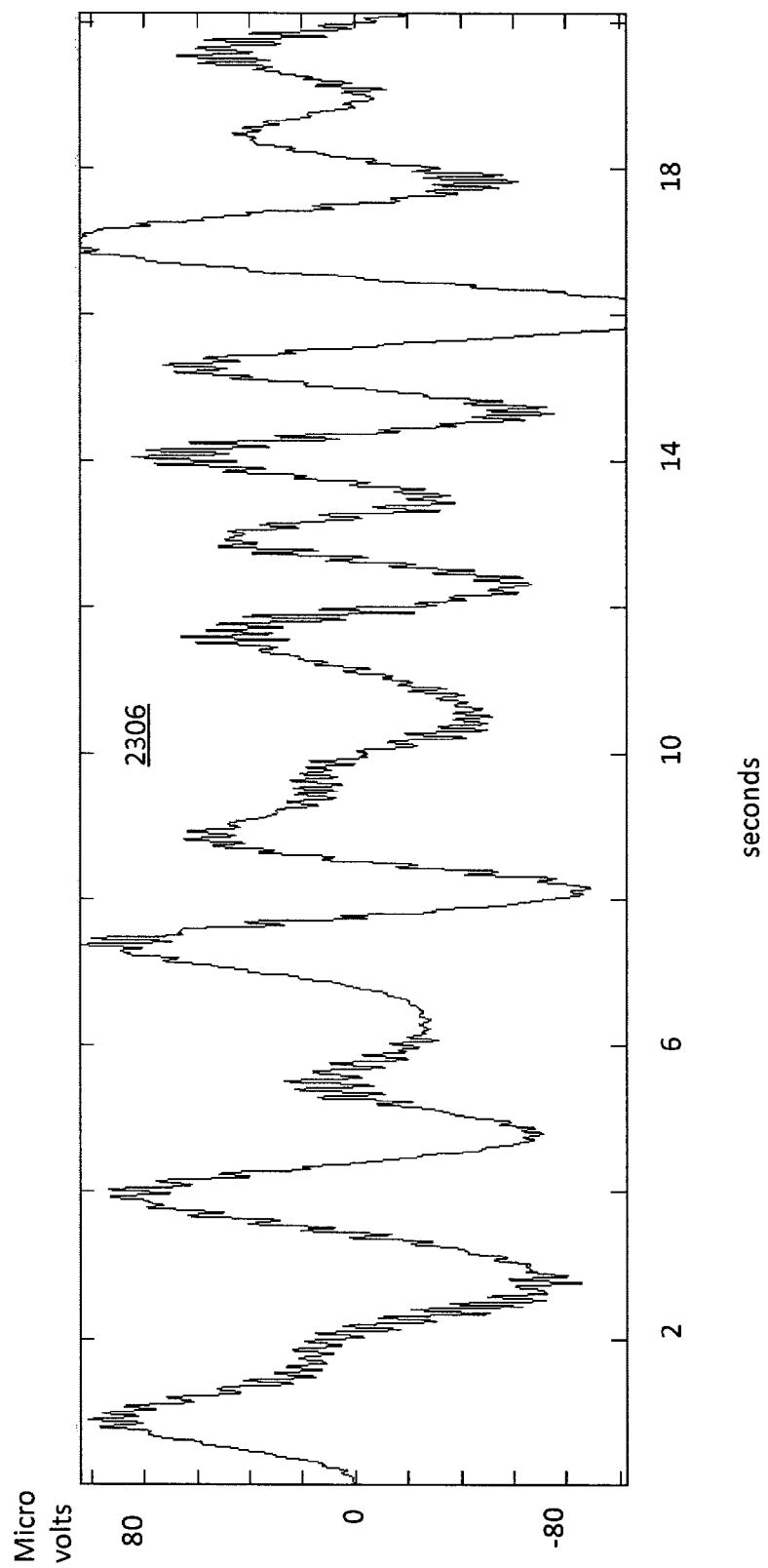
Figure 27:
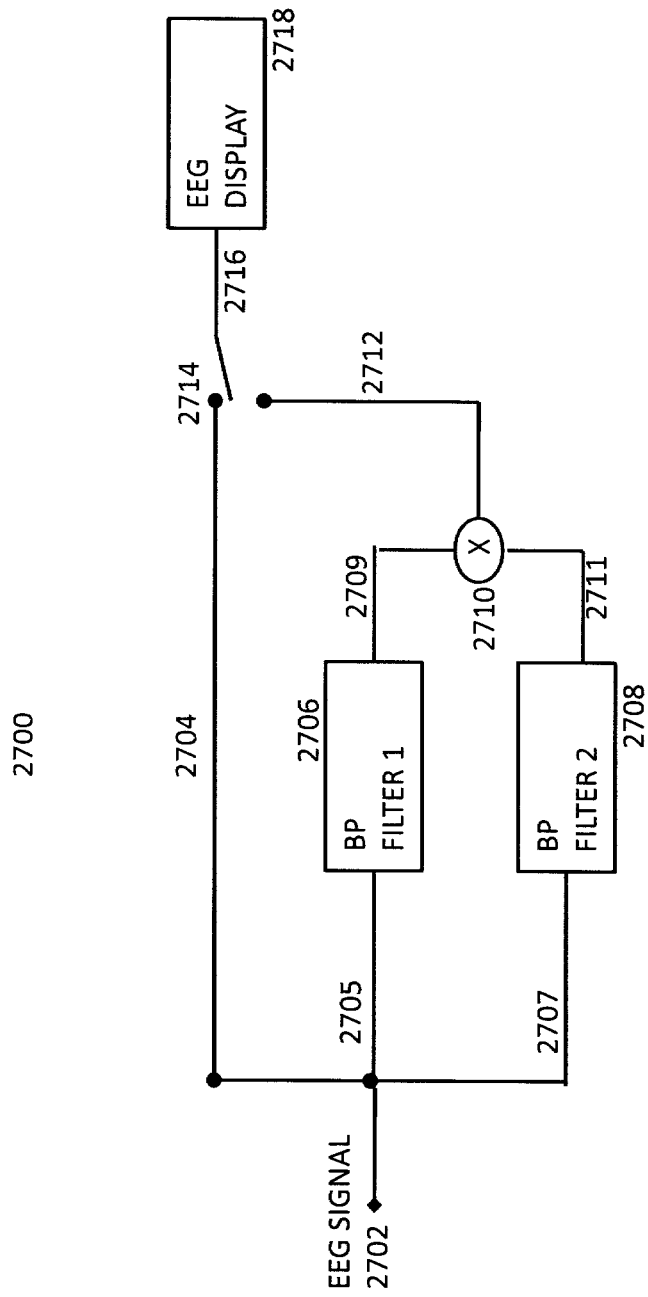
FIG. 27 illustrates a device for combining signals and displaying them in accordance with the principles of the present invention.

FIGS. 23-26 are a group of figures illustrating the individual signals useful for generating an example combined signal in accordance with the principles of the present invention. FIG. 23 illustrates a raw EEG signal 2300 in the time domain. FIG. 24 illustrates a filtered signal 2302 of the signal 2300 of FIG. 23 after passing through a bandpass filter of about 7-14 Hz. FIG. 25 illustrates a filtered signal 2304 of the signal 2300 of FIG. 23 after passing through a bandpass filter of about 0-4 Hz. FIG. 26 illustrates a combined signal 2306 generated by mixing, adding, or combining, the individual filtered band signals 2302 and 2304. The signal of FIG. 26 includes at least two components mixed with one another (i.e., the two signals modulate each other). One component 2304 is the raw EEG signal filtered in the 0.1 to 1.0 Hz range and a second component 2302 is the raw EEG signal filtered in the 7-14 Hz range.

FIG. 28A-28F illustrate four different EEG spectra and their resulting respective, combined signals in accordance with the principles of the present invention. In particular, each combined signal is generated using an EEG signal band pass filtered between about 0-1.5 Hz (±0.5 Hz) and the same EEG signal band pass filtered between about 7-14 Hz (±1.0 Hz).

Figure 28A:
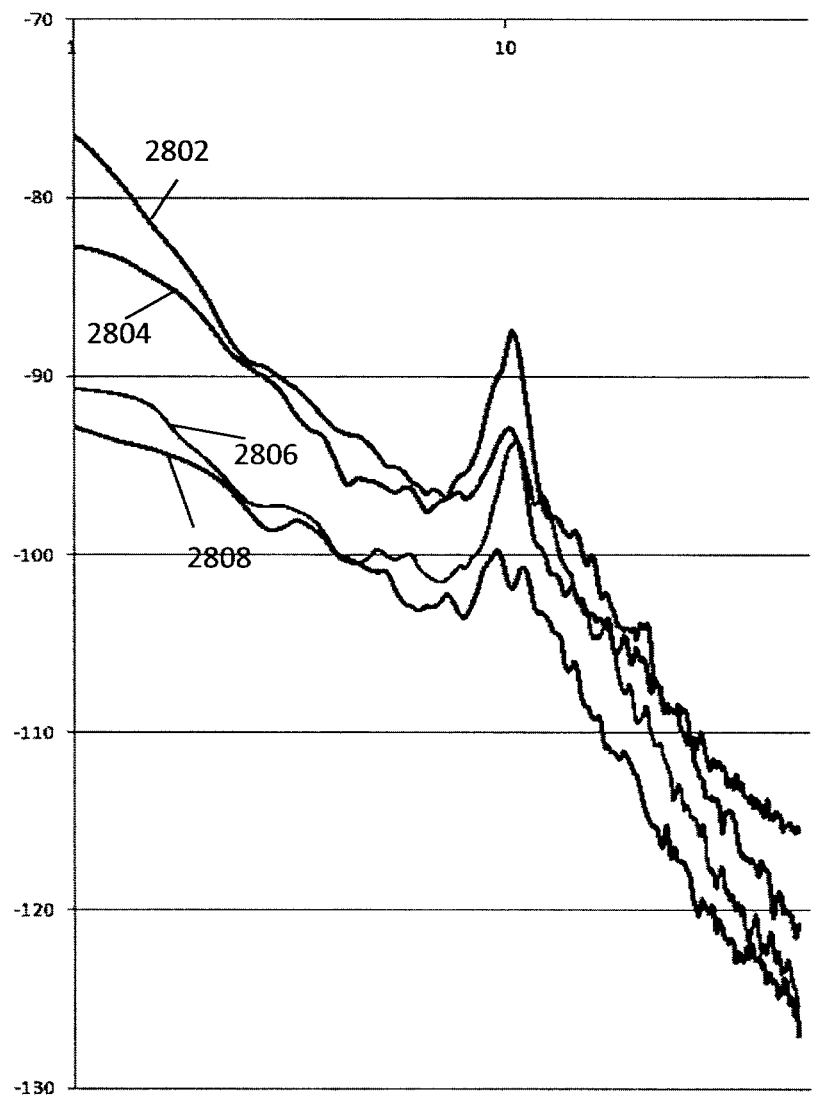
FIG. 28A-28F illustrate four different EEG spectra and their resulting respective, combined signals in accordance with the principles of the present invention.

In FIG. 28A, four different EEG log-log spectra are shown 2802, 2804, 2806, 2808 that is constructed from about 1 to 3 minutes of EEG signal. As explained below, FIGS. 28B, 28C, 28E and 28F are each a combined, or mixed, signal constructed from 20 seconds of EEG signal, wherein the 20 second window begins at different time points during a patient's procedure. For example, the EEG data for the mixed signal of FIG. 28B starts at the time point "1 minute" and extends for "20 seconds". The EEG data for the mixed signal of FIG. 28C starts at the time point "17 minutes" and also extends for "20 seconds". The length of time, 20 seconds, is merely exemplary and displays with shorter or longer sections of the mixed signal can be used without departing from the scope of the present invention. The signal of FIG. 28D is the same underlying signal as that of FIG. 28C but displayed in a different vertical scale.

Figure 28B:
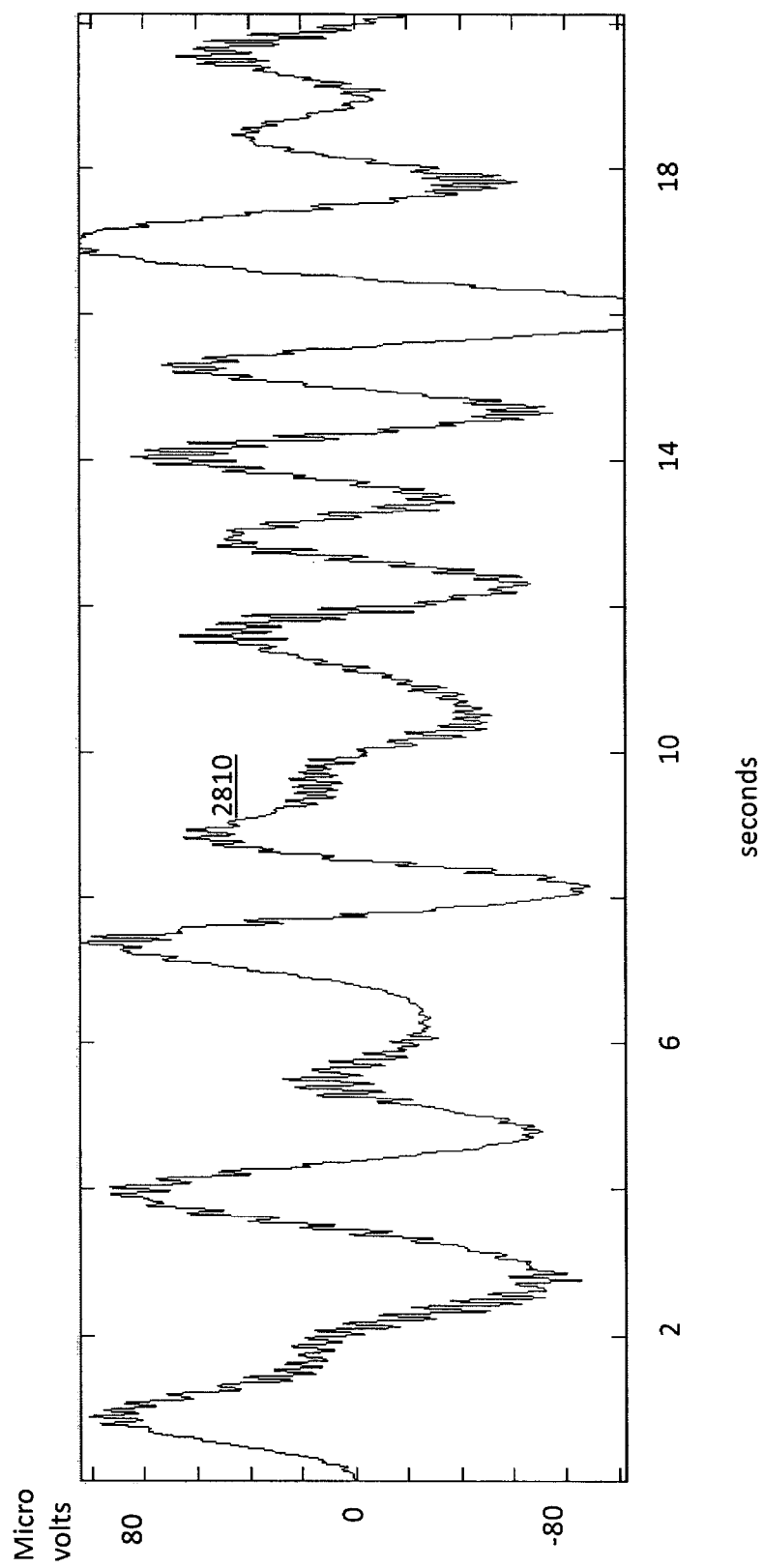
Figure 28C:
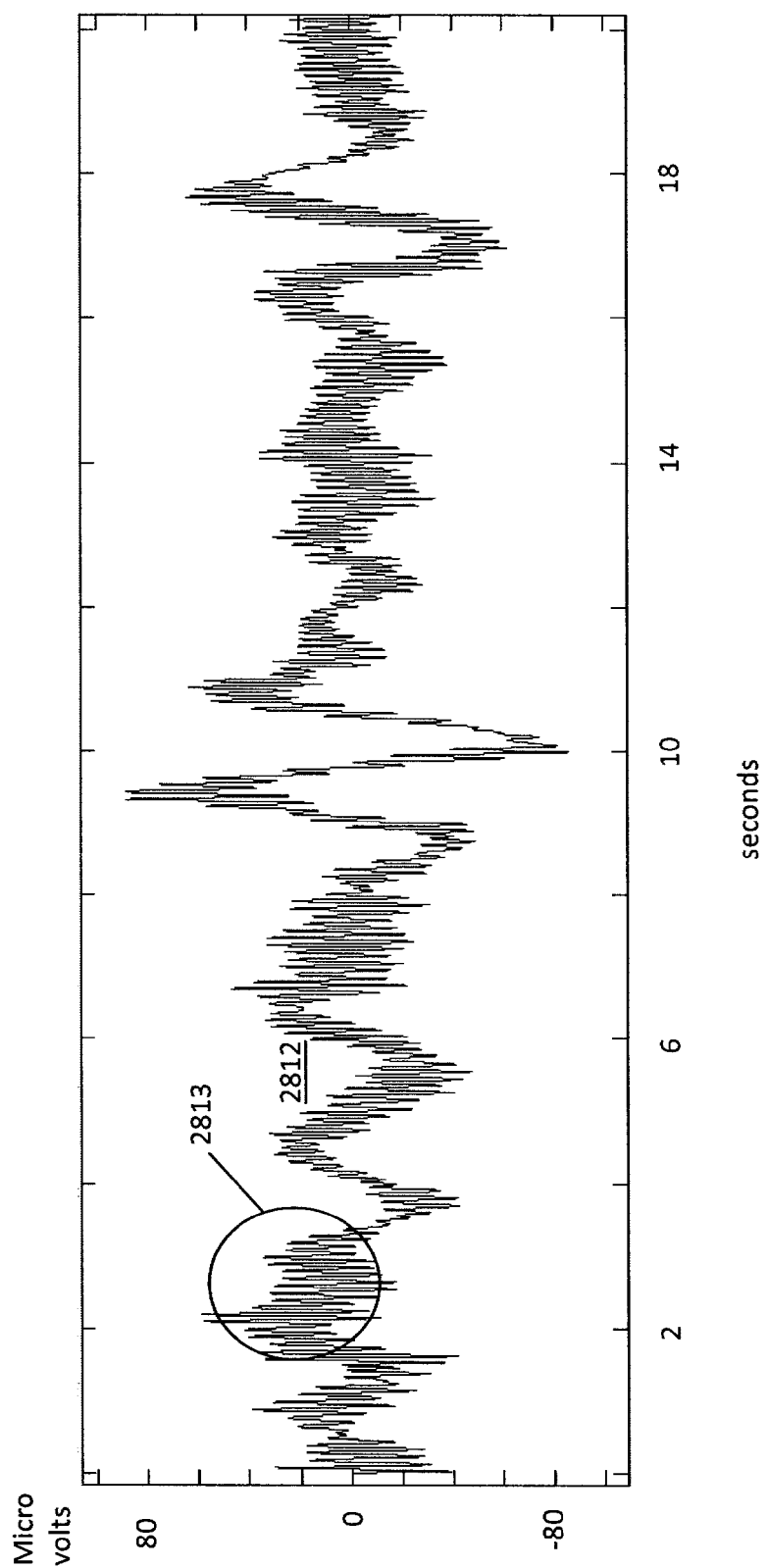
Figure 28D:
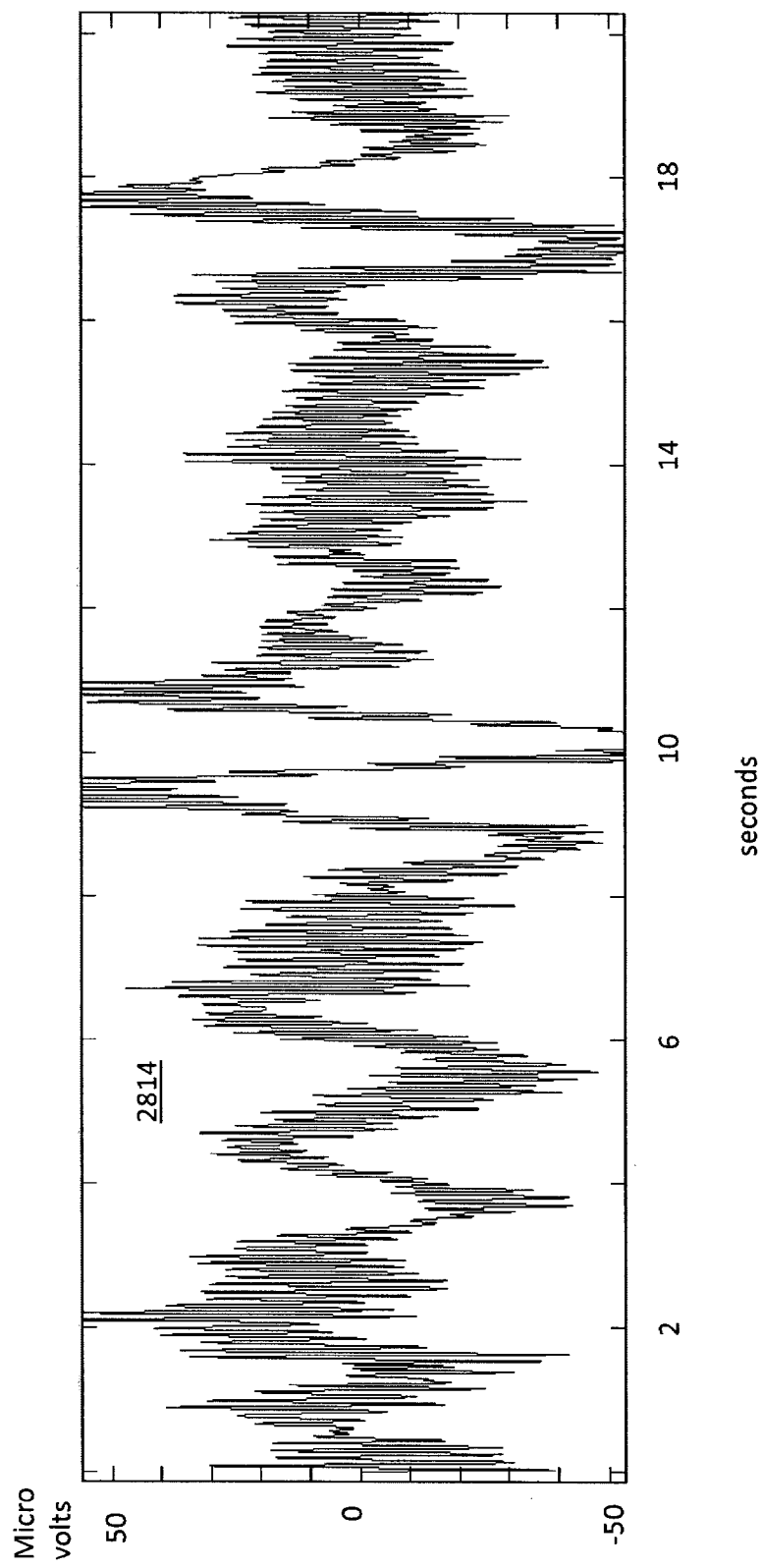

FIG. 28B illustrates a combined signal 2810 of the EEG signal used, in part, to construct the spectrum 2802. Relative to the other spectra, the spectrum 2802 has more activity around 1 Hz. The combined signal 2812 of FIG. 28C is a result of the EEG signal that is used, in part, to generate the spectra 2804. As can be seen from the presence of the oscillations 2813 and the lower amplitude range of the mixed signal 2812 (as compared to signal 2810), the spectrum 2804 includes relatively less activity around 1 Hz but more spindle activity around 10 Hz. FIG. 28D shows the combined signal 2812 on a different scale (e.g., ±50 rather than ±100) to more clearly convey the reduction in activity around 1 Hz so that each of the two important oscillations can be easily visualized.

Figure 28E:
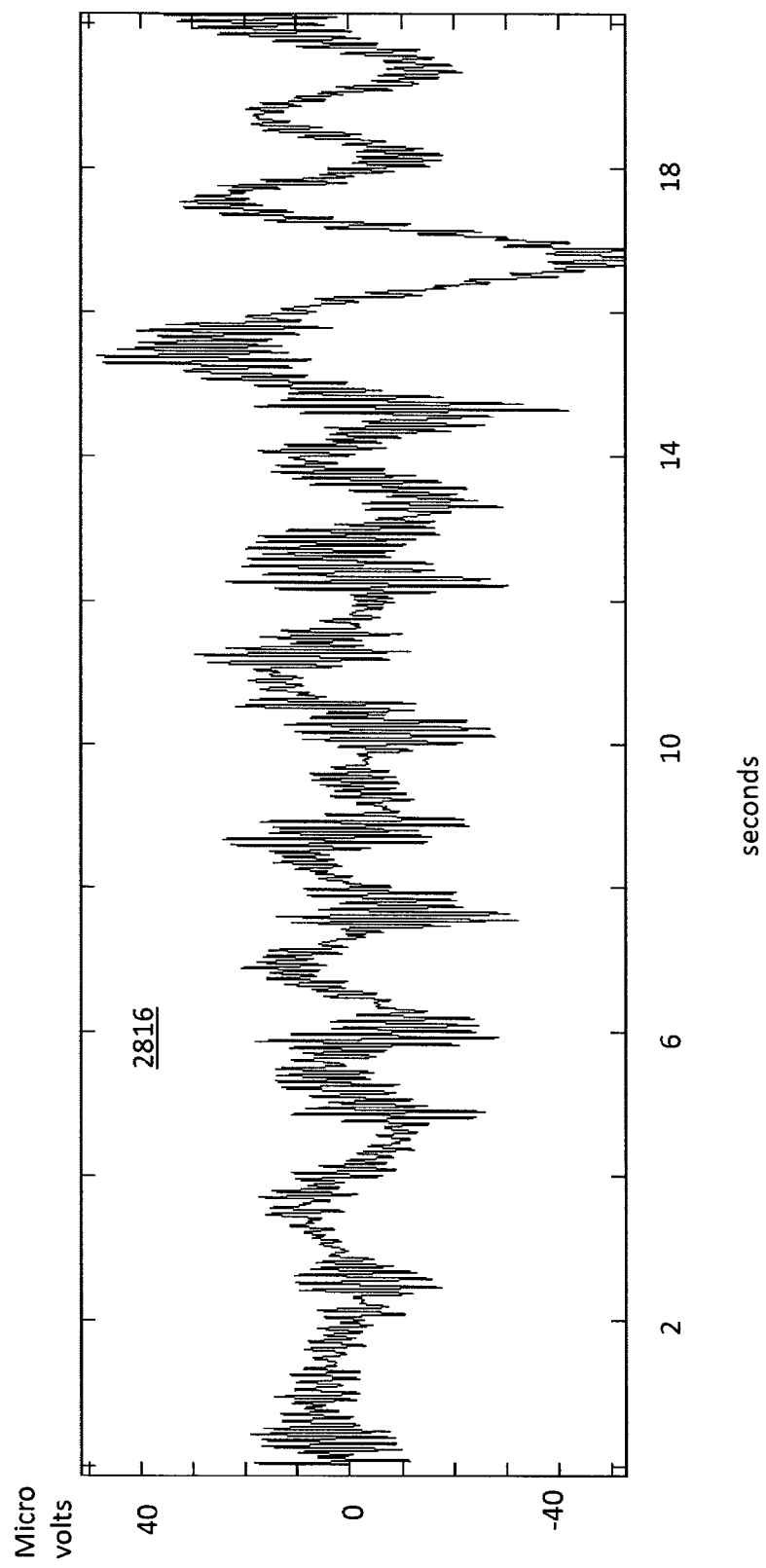
Figure 28F:
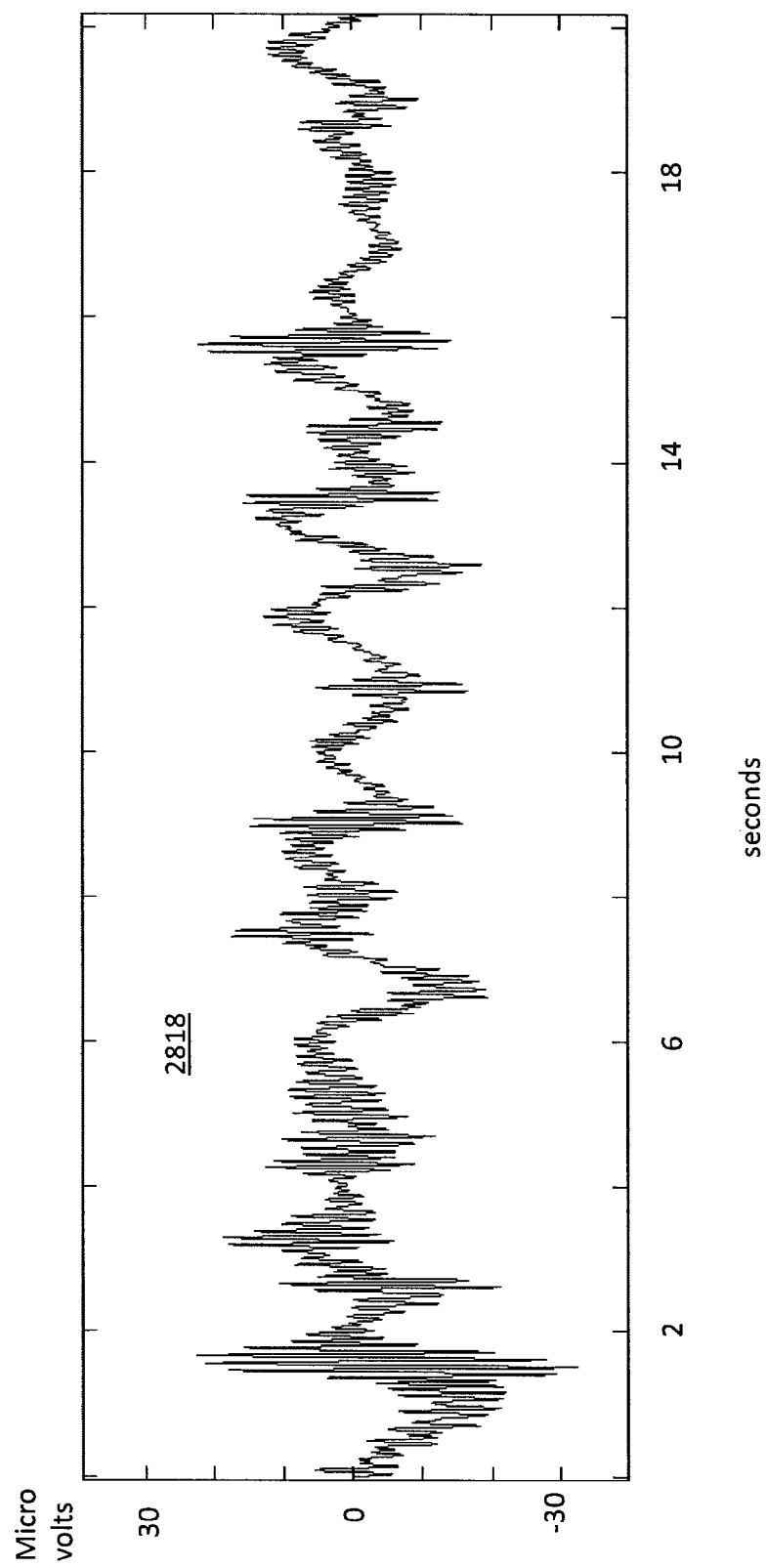

FIG. 28E illustrates a combined signal 2816 of the EEG signal used to construct the spectrum 2806. The mixed signal 2816 shows, in the time domain, that there is less activity in the lower frequency band and the higher frequency band as compared to the spectrum 2804. FIG. 28F illustrates a combined signal 2818 of the EEG signal used to construct the spectrum 2808 with a further reduction of the scale used in displaying the mixed signal 2818 (e.g., ±40). The mixed signal 2818 shows, in the time domain, there is even less activity in the lower frequency band and the higher frequency band as compared to the spectrum 2806. Not only is the time domain data of the mixed signals being displayed in near real time, the reduction or increase of activity in a frequency band can be easily recognized.

Embodiments of the present invention also contemplate a display that can include a density spectral array (DSA) with a power scale adjusted to best indicate when the EEG spectrum is at a reference point and indicate changes in the amplitude and shape of the EEG spectra above or below that level. Current EEG DSA plots have a fixed scale that is the same for all patients. U.S. Pat. No. 7,395,292 to Johnson includes a description of conventional CSA and DSA displays and is incorporated herein by reference in its entirety.

Figure 29:
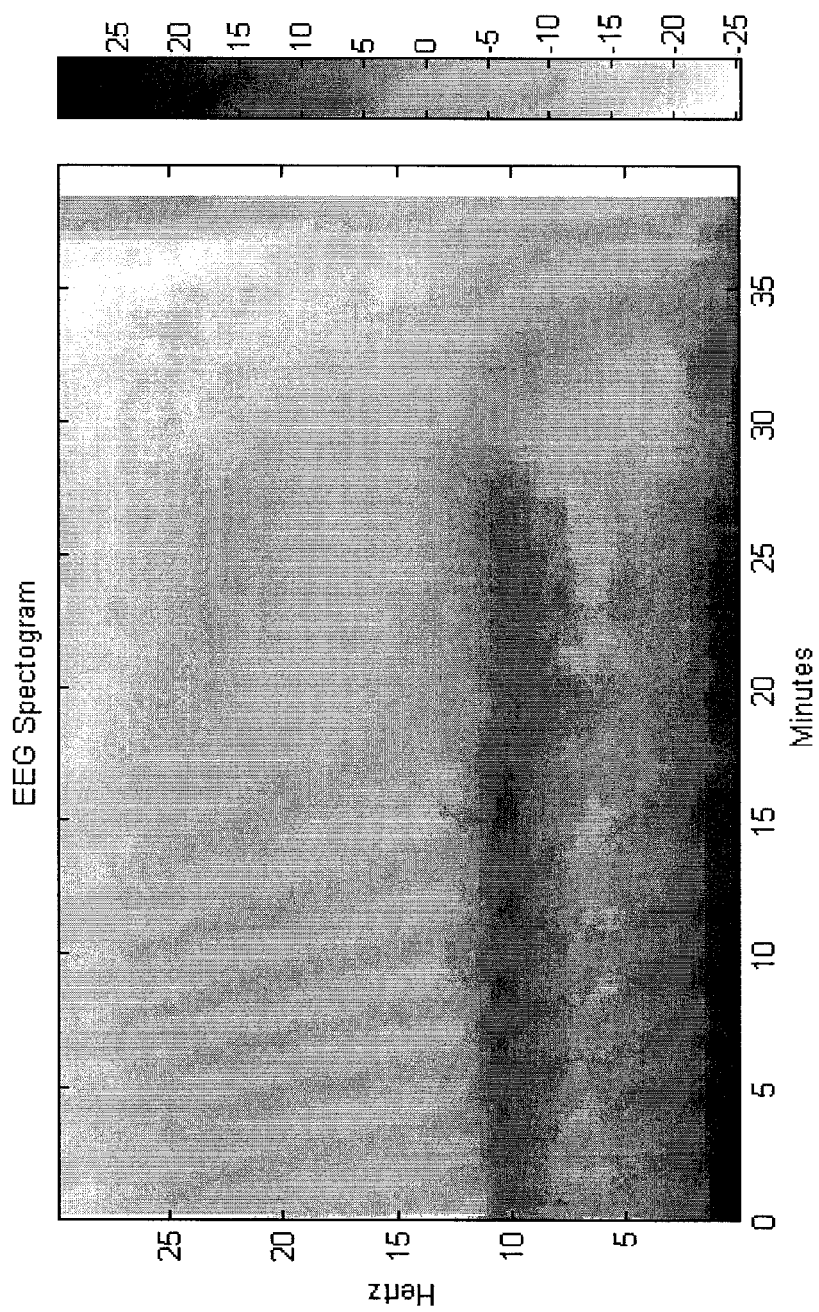
FIG. 29 illustrates a conventional DSA.

A conventional DSA display, such as FIG. 29, can be used to show long term trends and sudden changes from periods of an unchanging signal. A conventional DSA typically has a linear time scale as the horizontal axis and a linear frequency scale as the vertical axis. However, these axes can be flipped as well. The intensity, or gray scale value, of a displayed point represents an amplitude (e.g., power) of a particular frequency for the spectrum at a particular point in time. As time passes, data from new spectra are displayed to the right of previous spectra.

There are many problems with current DSA displays in EEG monitors for anesthesia, however. For example, an ordinary auto scale based entirely on adjusting the scale of the graph to match the amplitude range of the signal may not show details of the peaks and troughs well. Another problem would be that the data may start out with a low range of amplitude and change to a higher range.

Accordingly, embodiments of the present invention relate to a DSA display that adjusts its scale based on maximizing a dynamic range between a theta trough and the alpha and delta peaks. The display could involve a "pseudo DSA" plot which contains elements of a DSA display along with modifications that indicate features of the spectra. It is difficult to appreciate changing slope and amplitude of a straight or curved line with a standard DSA plot. The EEG spectra in an anesthetized patient from 15 to 45 Hz is a down sloping curved line in a log-linear plot and a steeply sloped straight line in a log-log plot. The amplitude and slope of this section could be indicated with display elements other than the amplitude at each frequency.

Figure 30A:
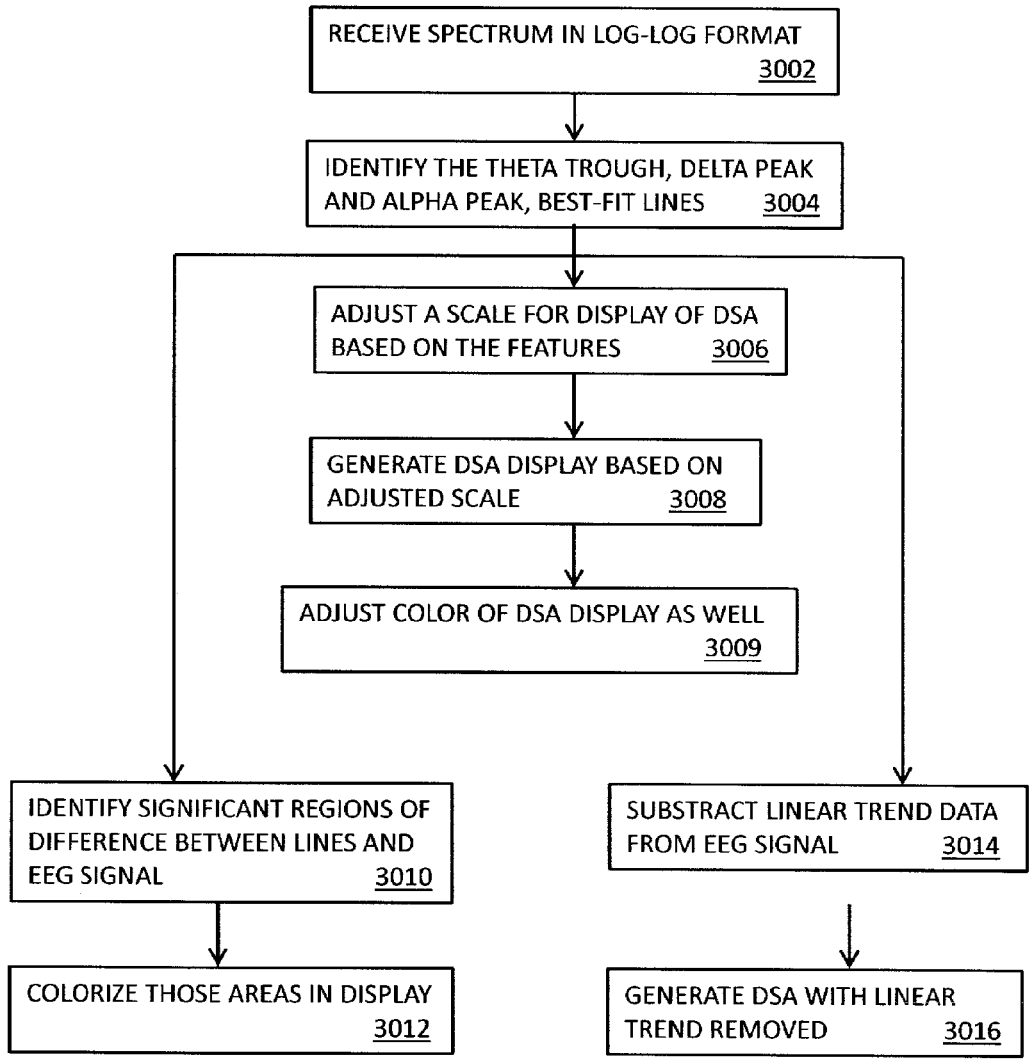

An EEG display device in accordance with the principles of the present invention could operate in accordance with the method of FIG. 30A. The display device can receive an EEG signal or EEG spectrum, in step 3002 and extract, in step 3004, the relevant features of the shape of the spectrum as explained in the above-mentioned and incorporated patents and patent applications. Example features can include a theta trough as well as a delta peak and an alpha peak. Rather than a simple autoscale feature based on the spectra, the lowest of these extracted values and the highest of these extracted values (in terms of power amplitude) are used to define the scale for displaying DSA data, in step 3006. Ultimately in step 3008, the DSA is displayed utilizing the adjusted scale.

An alternative improvement is to augment a DSA to something that looks like a DSA but is constructed to show the most relevant features that create the shape of the spectra. For example, this augmented DSA display can show only the peaks and troughs by drawing the approximation lines 104, 106 (as shown in FIG. 30B) and color, or otherwise visually distinguish, the areas 3050, 3052 of the spectrum 100 that are above the lines 104, 106. Returning to the flowchart of FIG. 30A, the display apparatus can extract the best-fit lines in step 3004, then, in step 3010, identify regions of the spectrum above the best-fit lines so that, in step 3012, the best fit lines, the spectrum and the significant regions can all be displayed.

Figure 30C:
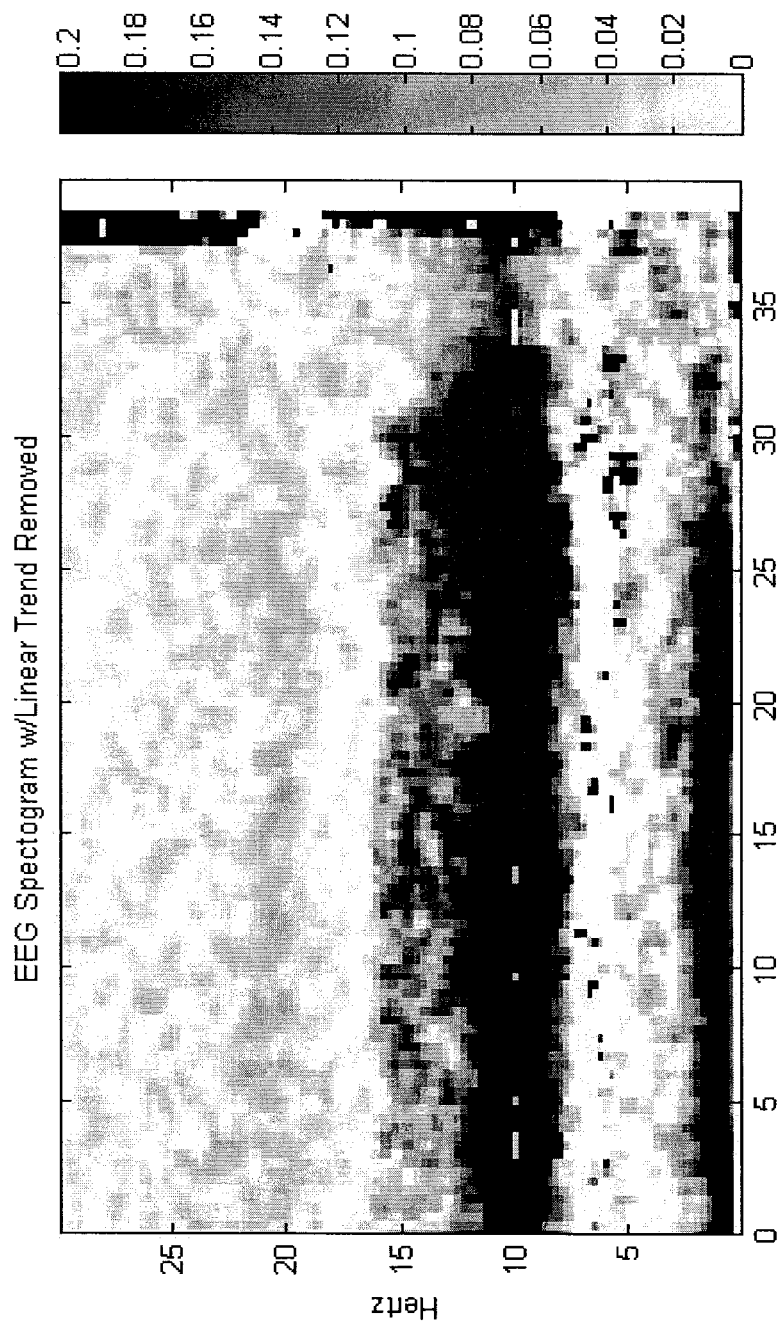
Figure 30D:
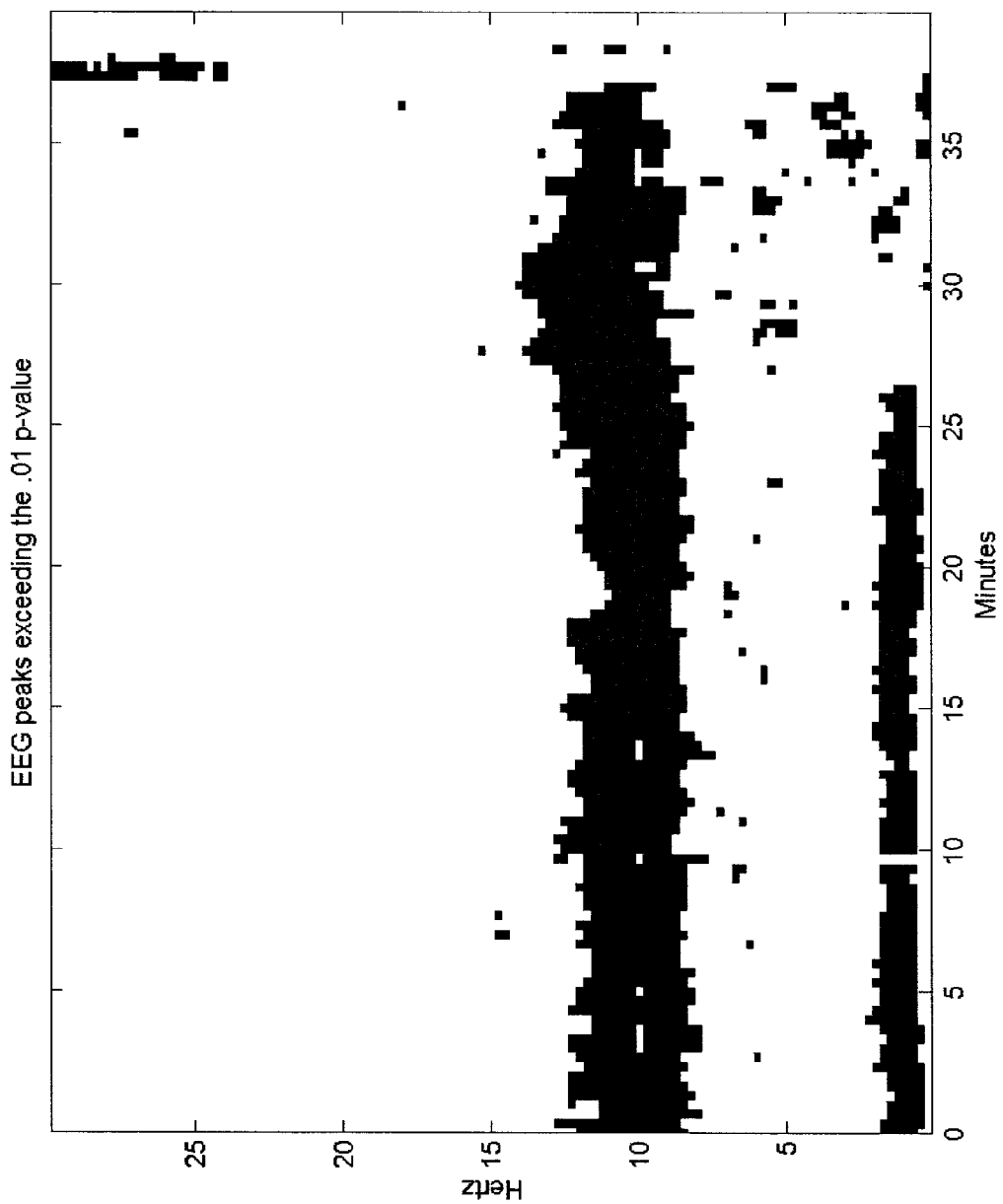

Alternatively, the contribution to the DSA that is attributable to the best-fit lines (i.e., the linear trend of the spectrum) can be subtracted out so only the difference is displayed such as, for example, is illustrated in FIG. 30C. This alternative is shown as steps 3014 and 3016 of FIG. 30A. Similarly, another augmented DSA can display those areas above the approximations lines that are sufficiently far enough to pass a probability test. FIG. 30D shows an augmented DSA that shows only the areas that are sufficiently far enough above the two approximations lines to not be due to random chance. For example, more than a 10% deviation (as measured in terms of the log nature of the scale) may be statistically significant. However, one of ordinary skill will recognize other amounts of deviation (e.g., about 1% to upwards of 50%) may be selected as an indication of "statistically significant".

The method described above with respect to autoscaling can be further modified as shown in step 3009 to add a colorizing component to the displayed DSA. In particular, a color range for the troughs and peaks designed to directly indicate their amplitude values and indirectly the relative heights of the peaks can be utilized. For example, when the maximum alpha peak occurs, the scale of the display will show the trough at one color in the range that is always the same color regardless of whether this is a high, normal, or low amplitude EEG signal. Then the color changes going up the peaks. The user will easily recognize where the patient is on the progression of spectra by seeing a pattern to the color scheme that is familiar. This arrangement shows more valuable information than multiplying by the frequency to an exponential value.

The second part of the spectra is at higher frequencies than the alpha peak. Usually that is a straight line on a log-log graph. The slope of this line is often the only relevant feature in this part of the spectra. It is difficult to tell the slope of the line that is the spectra with a DSA. The user must notice the rate that the dots of a grey scale get further apart (or colors change) as the amplitude declines and try to visualize the slope of the line. A DSA is usually shown with a log-linear (linear frequency scale). With this arrangement this part of the spectra is a curved line. It is very hard to determine the "slope" of a curved line with a DSA plot. A DSA plot that uses a log-log scale would be easier to interpret.

A further improvement is to show this part of the spectra as a single color. That color changes to indicate the slope of the high frequency approximation line. If there is an area that is above the approximation line such as a beta peak or a gamma band increase, this can be indicated with a separate color scheme. Combining the improvements for the features of both the low and high frequency regions will create a "pseudo" DSA display which is much more useful.

As discussed above, a DSA-like display could be provided in which the minimum amplitude on the scale is the theta trough and the maximum amplitude on the scale is either the delta or alpha peak. Alternatively, the scale could have its lower limit set at the lowest point on the low frequency approximation line. In at least some embodiments described in the above-identified and incorporated patents and applications, there may be a third line under the alpha peak. This third line can be substantially horizontal and extend from a right-most edge of the low frequency best-fit line to the left-most edge of the high frequency best-fit line. Instead of setting the lowest limit of the scale based on the theta trough or the low frequency best-fit line, it could be set based on "the highest point on the high-frequency approximations line(s)". The intersection of the high-frequency line with the next line of lower frequency can also be referred to as the "spectral edge". Essentially, a DSA-like display can be provided for areas of the spectra of lower frequency than the spectral edge. This will provide good resolution of the peaks of the spectra.

As mentioned, the display scale for the DSA can, for example, be between 0 to 100 and correspond to a gray level (i.e., entirely white to entirely black) or pixel intensity or pixel color. In the above discussion about setting the lower and upper limits, the lower limit could be set based on the power value at the theta trough, the power value at the lowest point on the low frequency approximation line, or the power value at the highest point on the high frequency approximation line. For example the "30" value (on the scale of 0 to 100) could be set to correspond to one of the power values just mentioned. Thus, if a subsequent spectrum includes a power value below that "30" value, it can still be displayed in a way that is visually distinguishable (i.e., that power value can be displayed with a value between 0 and 29). Similarly, the upper limit can be set based on the power value at the alpha peak such that the alpha peak power value corresponds to an "80" value on the display scale. Subsequent power values that might be encountered that would correspond to a display above the "80" value, can still be displayed in a visually distinctive manner (i.e., the subsequent power value can be displayed with a value between 81 and 100). As such, attributes of the spectrum and/or the approximation lines can be associated with different values on the display scale and then power values corresponding to an upper limit (e.g., "100") and a lower limit (e.g., "0") can be extrapolated based on those attributes.

One complication to address is that the trough point amplitude and the high-frequency line intersection point amplitude typically changes during the surgery. In general, spectra can be analyzed to determine whether the high-frequency approximation line slopes down steeply and there are few deviations from that line. (See, for example, incorporated patents and applications describing "red", "yellow", "green" slopes.) If so, the pattern will match at least one template that we can identify. Using the matching template, data about the patient, and a current anesthetic level, a preliminary determination may be made as to where the current spectrum is in the normal progression. Additional spectra can be acquired after changing the level of anesthesia. When the system or operator believes a reference point such as the maximum alpha peak point has been located, then a color scheme scale can be set. There could be a standard color for the trough point or the alpha peak so that when the amplitude changes the colors change and an observer of the display can be provided visual information that will allow them to recognize this as either a pattern of more or less anesthesia than the selected reference spectra.

For the area of higher frequency than the spectral edge it can be beneficial to indicate the slope of the high-frequency approximation line with a single color for the entire frequency range. As mentioned above, if there are any peaks or deviations they can be indicated with a separate color scheme. This could all be done with either subtracting the approximation lines and working with what is left, or finding a trough point, peak points, and the "spectral edge" and doing a DSA with a scale adjusted to those points.

Another contemplated possibility is to use a log scale for the frequency axis of the DSA display. This stretches out the low frequency area which has the important, or "more interesting", features and compresses the high frequency area which has few features of interest. There could, alternatively, be two frequency zones, each with their own frequency scale. There would be one scale for frequencies between about 0 to 15 or 20 Hz which is stretched and another for 20 to 45 Hz which is more compressed as compared with the scale for the lower frequencies.

In the above discussion, the term amplitude is intended to include power and anything mathematically related to amplitude.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method for providing an indication of a state of awareness for a patient, comprising:
   arranging data of an EEG power spectrogram to provide power versus frequency in a log-log arrangement;
   calculating a first best-fit line for a lower frequency region of the EEG power spectrogram, using a processor;
   calculating a second best-fit line for a higher frequency region of the EEG power spectrogram, using said processor; and
   displaying, on a display device, a density spectral array of the spectrogram using a display scale that ranges between an upper limit and a lower limit, wherein the lower limit is set based on one of the first best-fit line and the second best-fit line and the upper limit is set based on one of an alpha peak or a delta peak of the EEG power spectrogram.

2. The method of claim 1, wherein the lower limit is set based on a highest point of the second best-fit line.

3. The method of claim 1, wherein the lower limit is set based on a lowest point of the first best-fit line.

4. The method of claim 1, wherein the lower limit is set based on a theta trough of the power spectrogram.

5. The method of claim 1, wherein the display scale varies in terms of one of color, display intensity, gray scale value.

6. An apparatus for providing an indication of a state of awareness for a patient, comprising:
   a data formatter configured to arrange data of an EEG power spectrogram power spectrogram, that provides power versus frequency, in a log-log arrangement;
   a first calculator configured to calculate a first best-fit line for a lower frequency region of the EEG power spectrogram;
   the first calculator also configured to calculate a second best-fit line for a higher frequency region of the EEG power spectrogram;
   a display configured to provide a density spectral array of the spectrogram using a display scale that ranges between an upper limit and a lower limit, wherein the lower limit is set based on one of the first best-fit line and the second best-fit line and the upper limit is set based on one of an alpha peak or a delta peak of the EEG power spectrogram.

7. The apparatus of claim 6, wherein the lower limit is set based on a highest point of the second best-fit line.

8. The apparatus of claim 6, wherein the lower limit is set based on a lowest point of the first best-fit line.

9. The apparatus of claim 6, wherein the lower limit is set based on a theta trough of the power spectrogram.

10. The apparatus of claim 6, wherein the display scale varies in terms of one of color, display intensity, gray scale value.

11. A method for providing an indication of a state of awareness for a patient, comprising:
    arranging data of an EEG power spectrogram to provide power versus frequency in a log-log arrangement;
    calculating a first best-fit line for a lower frequency region of the EEG power spectrogram, using a processor;
    calculating a second best-fit line for a higher frequency region of the EEG power spectrogram, using said processor;
    determining, by the processor, differences between the EEG power spectrogram and the first and second best-fit lines; and
    displaying, on a display device, a density spectral array of the EEG power spectrogram, with values calculated based on the differences between the EEG power spectrogram and the first and second best-fit lines, wherein the differences are determined by subtracting the first and second best-fit lines from the EEG power spectrogram to determine a respective difference value at each frequency value of the EEG power spectrogram.

12. The method of claim 11, wherein displaying the differences comprises:
    defining a display graph with a horizontal axis representing time and a vertical axis representing frequency; and
    setting a respective display intensity for each respective difference value, wherein the display intensity ranges between an upper limit and a lower limit.

13. The method of claim 11, wherein determining differences comprises:
    determining if each respective difference value exceeds a predetermined threshold; and
    displaying those respective difference values which exceed the predetermined threshold.

14. The method of claim 11, wherein determining differences comprises:
    determining at which frequencies the EEG spectrogram exceeds a corresponding one of the first and second best-fit lines.

15. An apparatus for providing an indication of a state of awareness for a patient, comprising:
    a data formatter configured to arrange data of an EEG power spectrogram power spectrogram, that provides power versus frequency, in a log-log arrangement;
    a first calculator configured to calculate a first best-fit line for a lower frequency region of the EEG power spectrogram;
    the first calculator also configured to calculate a second best-fit line for a higher frequency region of the EEG power spectrogram;
    the first calculator also configured to calculate differences between the EEG power spectrogram and the first and second best-fit lines; and
    a display device configured to display a density spectral array of the EEG power spectrogram, with values calculated based on the differences between the EEG power spectrogram and the first and second best-fit lines, wherein the differences are determined by subtracting the first and second best-fit lines from the EEG power spectrogram to calculate a respective difference value at each frequency value of the EEG power spectrogram.

16. The apparatus of claim 15, wherein display device is also configured to display:
    a display graph with a horizontal axis representing time and a vertical axis representing frequency; and
    a respective display intensity for each respective difference value, wherein the display intensity ranges between an upper limit and a lower limit.

17. The apparatus of claim 15, wherein the calculation of differences comprises:
    determining if each respective difference value exceeds a predetermined threshold; and
    displaying those respective difference values which exceed the predetermined threshold.

18. The apparatus of claim 15, wherein the calculation of differences comprises:
    determining at which frequencies the EEG spectrogram exceeds a corresponding one of the first and second best-fit lines.

* * * * *